(12) United States Patent  
Weber

(10) Patent No.: US 8,840,660 B2
(45) Date of Patent: Sep. 23, 2014

(54) BIOERODIBLE ENDOPROSTHESES AND METHODS OF MAKING THE SAME

(75) Inventor: Jan Weber, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 574 days.

(21) Appl. No.: 11/327,149

(22) Filed: Jan. 5, 2006

(65) Prior Publication Data

US 2007/0156231 A1    Jul. 5, 2007

(51) Int. Cl.
  *A61F 2/06* (2013.01)
  *A61L 31/02* (2006.01)
  *A61L 31/14* (2006.01)
  *A61F 2/82* (2013.01)

(52) U.S. Cl.
  CPC ........... *A61F 2/82* (2013.01); *A61F 2250/0054* (2013.01); *A61L 31/022* (2013.01); *A61F 2250/003* (2013.01); *A61L 31/148* (2013.01); *A61F 2210/0004* (2013.01); *A61F 2250/0037* (2013.01)
  USPC ........................................................ 623/1.38

(58) Field of Classification Search
  USPC ............ 623/1.38, 1.44, 1.46, 1.15, 1.16, 1.42
  See application file for complete search history.

(56) References Cited

U.S. PATENT DOCUMENTS

| | | |
|---|---|---|
| 2,950,187 A | 8/1960 | Ototani |
| 3,560,362 A | 2/1971 | Kasamatsu et al. |
| 3,569,660 A | 3/1971 | Houldcroft |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,002,877 A | 1/1977 | Banas |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |
| 4,585,652 A | 4/1986 | Miller et al. |
| 4,634,502 A | 1/1987 | Callahan et al. |

(Continued)

FOREIGN PATENT DOCUMENTS

| | | |
|---|---|---|
| AU | 739 507 | 11/1998 |
| AU | 2003 203 722 | 11/2003 |

(Continued)

OTHER PUBLICATIONS

Tian et al., "Corrosion resistance improvement of magnesium alloy using nitrogen plasma ion implantation", Surface & Coatings Technology, 198, pp. 454-458, 2005.

(Continued)

*Primary Examiner* — Kathleen Holwerda
*Assistant Examiner* — Sarah Simpson
(74) *Attorney, Agent, or Firm* — Fish & Richardson P.C.

(57) ABSTRACT

Endoprostheses are disclosed.

26 Claims, 7 Drawing Sheets

(56) References Cited

U.S. PATENT DOCUMENTS

| | | |
|---|---|---|
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,713,070 A | 12/1987 | Mano |
| 4,725,273 A | 2/1988 | Kira |
| 4,733,665 A | 3/1988 | Palmaz |
| 4,767,418 A | 8/1988 | Deininger et al. |
| 4,784,659 A | 11/1988 | Fleckenstein et al. |
| 4,800,882 A | 1/1989 | Gianturco |
| 4,804,382 A | 2/1989 | Turina et al. |
| 4,886,062 A | 12/1989 | Wiktor |
| 4,954,126 A | 9/1990 | Wallsten |
| 4,976,692 A | 12/1990 | Atad |
| 4,994,071 A | 2/1991 | MacGregor |
| 5,024,671 A | 6/1991 | Tu et al. |
| 5,059,211 A | 10/1991 | Stack et al. |
| 5,061,275 A | 10/1991 | Wallsten et al. |
| 5,061,914 A | 10/1991 | Busch et al. |
| 5,073,365 A | 12/1991 | Katz et al. |
| 5,079,203 A | 1/1992 | Pinnavaia |
| 5,091,024 A | 2/1992 | DeBold et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,195,969 A | 3/1993 | Wang et al. |
| 5,205,921 A | 4/1993 | Shirkanzadeh |
| 5,234,457 A | 8/1993 | Andersen |
| 5,236,413 A | 8/1993 | Feiring |
| 5,236,447 A | 8/1993 | Kubo et al. |
| 5,270,086 A | 12/1993 | Hamlin |
| 5,279,292 A | 1/1994 | Baumann et al. |
| 5,290,585 A | 3/1994 | Elton |
| 5,292,558 A | 3/1994 | Heller et al. |
| 5,302,414 A | 4/1994 | Alkhimov et al. |
| 5,304,121 A | 4/1994 | Sahatjian |
| 5,304,195 A | 4/1994 | Twyford, Jr. et al. |
| 5,306,286 A | 4/1994 | Stack et al. |
| 5,314,453 A | 5/1994 | Jeutter |
| 5,322,520 A | 6/1994 | Milder |
| 5,342,348 A | 8/1994 | Kaplan |
| 5,348,553 A | 9/1994 | Whitney |
| 5,356,433 A | 10/1994 | Rowland et al. |
| 5,360,440 A | 11/1994 | Andersen |
| 5,366,504 A | 11/1994 | Andersen et al. |
| 5,380,298 A | 1/1995 | Zabetakis et al. |
| 5,383,935 A | 1/1995 | Shirkhanzadeh |
| 5,385,776 A | 1/1995 | Maxfield et al. |
| 5,397,307 A | 3/1995 | Goodin |
| 5,405,367 A | 4/1995 | Schulman et al. |
| 5,421,955 A | 6/1995 | Lau et al. |
| 5,439,446 A | 8/1995 | Barry |
| 5,443,458 A | 8/1995 | Eury |
| 5,443,496 A | 8/1995 | Schwartz et al. |
| 5,443,500 A | 8/1995 | Sigwart |
| 5,449,373 A | 9/1995 | Pinchasik et al. |
| 5,449,382 A | 9/1995 | Dayton |
| 5,458,627 A | 10/1995 | Baranowski, Jr. et al. |
| 5,462,575 A | 10/1995 | Del Corso |
| 5,464,450 A | 11/1995 | Buscemi et al. |
| 5,464,650 A | 11/1995 | Berg et al. |
| 5,468,574 A | 11/1995 | Ehrenberg et al. |
| 5,474,797 A | 12/1995 | Sioshansi et al. |
| 5,492,763 A | 2/1996 | Barry et al. |
| 5,500,013 A | 3/1996 | Buscemi et al. |
| 5,514,154 A | 5/1996 | Lau et al. |
| 5,527,337 A | 6/1996 | Stack et al. |
| 5,536,573 A | 7/1996 | Rubner et al. |
| 5,545,208 A | 8/1996 | Wolff et al. |
| 5,549,664 A | 8/1996 | Hirata et al. |
| 5,551,954 A | 9/1996 | Buscemi et al. |
| 5,578,075 A | 11/1996 | Dayton |
| 5,587,200 A | 12/1996 | Lorenz et al. |
| 5,587,507 A | 12/1996 | Kohn et al. |
| 5,591,222 A | 1/1997 | Susawa et al. |
| 5,591,224 A | 1/1997 | Schwartz et al. |
| 5,599,352 A | 2/1997 | Dinh et al. |
| 5,603,556 A | 2/1997 | Klink |
| 5,605,696 A | 2/1997 | Eury et al. |
| 5,607,463 A | 3/1997 | Schwartz et al. |
| 5,609,629 A | 3/1997 | Fearnot et al. |
| 5,614,549 A | 3/1997 | Greenwald et al. |
| 5,624,411 A | 4/1997 | Tuch |
| 5,628,787 A | 5/1997 | Mayer |
| 5,629,077 A | 5/1997 | Turnlund et al. |
| 5,632,771 A | 5/1997 | Boatman et al. |
| 5,632,840 A | 5/1997 | Campbell |
| 5,649,951 A | 7/1997 | Davidson |
| 5,658,327 A | 8/1997 | Altman et al. |
| 5,672,242 A | 9/1997 | Jen |
| 5,674,192 A | 10/1997 | Sahatjian et al. |
| 5,674,242 A | 10/1997 | Phan |
| 5,676,685 A | 10/1997 | Razavi |
| 5,679,440 A | 10/1997 | Kubota |
| 5,690,670 A | 11/1997 | Davidson |
| 5,693,085 A | 12/1997 | Buirge et al. |
| 5,693,928 A | 12/1997 | Egitto et al. |
| 5,697,967 A | 12/1997 | Dinh et al. |
| 5,700,286 A | 12/1997 | Tartaglia et al. |
| 5,716,981 A | 2/1998 | Hunter et al. |
| 5,721,049 A | 2/1998 | Marcolongo et al. |
| 5,725,570 A | 3/1998 | Heath |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,749,880 A | 5/1998 | Banas et al. |
| 5,758,562 A | 6/1998 | Thompson |
| 5,759,192 A | 6/1998 | Saunders |
| 5,761,775 A | 6/1998 | Legome et al. |
| 5,769,883 A | 6/1998 | Buscemi et al. |
| 5,769,884 A | 6/1998 | Solovay |
| 5,773,925 A | 6/1998 | Kimura et al. |
| 5,776,184 A | 7/1998 | Tuch |
| 5,779,904 A | 7/1998 | Ruderman et al. |
| 5,780,807 A | 7/1998 | Saunders |
| 5,788,626 A | 8/1998 | Thompson |
| 5,788,687 A | 8/1998 | Batich et al. |
| 5,788,979 A | 8/1998 | Alt et al. |
| 5,797,898 A | 8/1998 | Santini, Jr. et al. |
| 5,800,511 A | 9/1998 | Mayer |
| 5,815,904 A | 10/1998 | Clubb et al. |
| 5,817,046 A | 10/1998 | Glickman |
| 5,824,045 A | 10/1998 | Alt |
| 5,824,048 A | 10/1998 | Tuch |
| 5,824,077 A | 10/1998 | Mayer |
| 5,830,217 A | 11/1998 | Ryan |
| 5,833,715 A | 11/1998 | Vachon et al. |
| 5,837,007 A | 11/1998 | Altman et al. |
| 5,837,275 A | 11/1998 | Burrell et al. |
| 5,840,387 A | 11/1998 | Berlowitz-Tarrant et al. |
| 5,843,089 A | 12/1998 | Sahatjian et al. |
| 5,843,172 A | 12/1998 | Yan |
| 5,852,277 A | 12/1998 | Gustafson |
| 5,854,382 A | 12/1998 | Loomis |
| 5,858,556 A | 1/1999 | Eckert et al. |
| 5,869,140 A | 2/1999 | Blohowiak et al. |
| 5,873,904 A | 2/1999 | Ragheb et al. |
| 5,876,756 A | 3/1999 | Takada et al. |
| 5,879,697 A | 3/1999 | Ding et al. |
| 5,880,661 A | 3/1999 | Davidson et al. |
| 5,882,335 A | 3/1999 | Leone et al. |
| 5,891,108 A | 4/1999 | Leone et al. |
| 5,891,191 A | 4/1999 | Stinson |
| 5,899,935 A | 5/1999 | Ding |
| 5,902,266 A | 5/1999 | Leone et al. |
| 5,906,759 A | 5/1999 | Richter |
| 5,907,893 A | 6/1999 | Zadno-Azizi et al. |
| 5,919,126 A | 7/1999 | Armini |
| 5,922,005 A | 7/1999 | Richter et al. |
| 5,922,021 A | 7/1999 | Jang |

(56) References Cited

U.S. PATENT DOCUMENTS

| | | |
|---|---|---|
| 5,928,247 A | 7/1999 | Barry et al. |
| 5,928,279 A | 7/1999 | Shannon et al. |
| 5,935,506 A | 8/1999 | Schmitz et al. |
| 5,938,903 A | 8/1999 | Broderick |
| 5,941,843 A | 8/1999 | Atanasoska et al. |
| 5,951,458 A | 9/1999 | Hastings et al. |
| 5,951,881 A | 9/1999 | Rogers et al. |
| 5,954,706 A | 9/1999 | Sahatjian |
| 5,957,975 A | 9/1999 | Lafont et al. |
| 5,958,440 A | 9/1999 | Burrell et al. |
| 5,961,547 A | 10/1999 | Razavi |
| 5,968,091 A | 10/1999 | Pinchuk et al. |
| 5,968,092 A | 10/1999 | Buscemi et al. |
| 5,972,027 A | 10/1999 | Johnson |
| 5,972,192 A | 10/1999 | Dubin et al. |
| 5,976,169 A | 11/1999 | Imran |
| 5,976,454 A | 11/1999 | Sterzel et al. |
| 5,977,204 A | 11/1999 | Boyan et al. |
| 5,980,554 A | 11/1999 | Lenker et al. |
| 5,980,564 A | 11/1999 | Stinson |
| 5,980,566 A | 11/1999 | Alt et al. |
| 6,001,125 A | 12/1999 | Golds et al. |
| 6,013,591 A | 1/2000 | Ying et al. |
| 6,017,553 A | 1/2000 | Burrell et al. |
| 6,017,577 A | 1/2000 | Hostettler et al. |
| 6,021,347 A | 2/2000 | Herbst et al. |
| 6,025,036 A | 2/2000 | McGill et al. |
| 6,027,742 A | 2/2000 | Lee et al. |
| 6,034,295 A | 3/2000 | Rehberg et al. |
| 6,042,597 A | 3/2000 | Kveen et al. |
| 6,056,776 A | 5/2000 | Lau et al. |
| 6,063,101 A | 5/2000 | Jacobsen et al. |
| 6,071,305 A | 6/2000 | Brown et al. |
| 6,080,190 A | 6/2000 | Schwartz |
| 6,086,773 A | 7/2000 | Dufresne et al. |
| 6,096,070 A | 8/2000 | Ragheb et al. |
| 6,096,175 A | 8/2000 | Roth |
| 6,099,561 A | 8/2000 | Alt |
| 6,099,562 A | 8/2000 | Ding et al. |
| 6,106,473 A | 8/2000 | Violante et al. |
| 6,107,004 A | 8/2000 | Donadio, III |
| 6,117,592 A | 9/2000 | Hoshino et al. |
| 6,120,260 A | 9/2000 | Jirele |
| 6,120,535 A | 9/2000 | McDonald et al. |
| 6,120,660 A | 9/2000 | Chu et al. |
| 6,123,861 A | 9/2000 | Santini, Jr. et al. |
| 6,132,463 A | 10/2000 | Lee et al. |
| 6,139,573 A | 10/2000 | Sogard et al. |
| 6,139,574 A | 10/2000 | Vacanti et al. |
| 6,139,913 A | 10/2000 | Van Steenkiste et al. |
| 6,140,740 A | 10/2000 | Porat et al. |
| 6,143,370 A | 11/2000 | Panagiotou et al. |
| 6,153,252 A | 11/2000 | Hossainy et al. |
| 6,159,142 A | 12/2000 | Alt |
| 6,162,238 A | 12/2000 | Kaplan et al. |
| 6,164,284 A | 12/2000 | Schulman et al. |
| 6,165,211 A | 12/2000 | Thompson |
| 6,167,307 A | 12/2000 | Hess |
| 6,168,602 B1 | 1/2001 | Ryan |
| 6,170,488 B1 | 1/2001 | Spillman, Jr. et al. |
| 6,174,329 B1 | 1/2001 | Callol et al. |
| 6,174,330 B1 | 1/2001 | Stinson |
| 6,180,222 B1 | 1/2001 | Schulz et al. |
| 6,185,455 B1 | 2/2001 | Loeb et al. |
| 6,185,457 B1 | 2/2001 | Kroll et al. |
| 6,190,404 B1 | 2/2001 | Palmaz et al. |
| 6,192,271 B1 | 2/2001 | Hayman |
| 6,201,991 B1 | 3/2001 | Chekanov |
| 6,203,536 B1 | 3/2001 | Berg et al. |
| 6,206,914 B1 | 3/2001 | Soykan et al. |
| 6,206,915 B1 | 3/2001 | Fagan et al. |
| 6,206,916 B1 | 3/2001 | Furst |
| 6,212,434 B1 | 4/2001 | Scheiner |
| 6,214,037 B1 | 4/2001 | Mitchell et al. |
| 6,214,042 B1 | 4/2001 | Jacobsen et al. |
| 6,217,607 B1 | 4/2001 | Alt |
| 6,228,445 B1 | 5/2001 | Tverberg |
| 6,231,597 B1 | 5/2001 | Deem et al. |
| 6,240,616 B1 | 6/2001 | Yan |
| 6,241,762 B1 | 6/2001 | Shanley |
| 6,245,103 B1 | 6/2001 | Stinson |
| 6,245,104 B1 | 6/2001 | Alt |
| 6,249,952 B1 | 6/2001 | Ding |
| 6,251,136 B1 | 6/2001 | Guruwaiya et al. |
| 6,251,980 B1 | 6/2001 | Lan et al. |
| 6,253,252 B1 | 6/2001 | Schofield |
| 6,253,443 B1 | 7/2001 | Johnson |
| 6,254,632 B1 | 7/2001 | Wu et al. |
| 6,258,117 B1 | 7/2001 | Camrud et al. |
| 6,264,687 B1 | 7/2001 | Tomonto |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,277,078 B1 | 8/2001 | Porat et al. |
| 6,280,385 B1 | 8/2001 | Melzer et al. |
| 6,280,411 B1 | 8/2001 | Lennox |
| 6,283,386 B1 | 9/2001 | Van Steenkiste et al. |
| 6,287,331 B1 | 9/2001 | Heath |
| 6,287,332 B1 | 9/2001 | Bolz |
| 6,287,335 B1 | 9/2001 | Drasler et al. |
| 6,287,628 B1 | 9/2001 | Hossainy et al. |
| 6,290,721 B1 | 9/2001 | Heath |
| 6,290,722 B1 | 9/2001 | Wang |
| 6,291,076 B1 | 9/2001 | Nakatsugawa |
| 6,299,604 B1 | 10/2001 | Ragheb et al. |
| 6,299,755 B1 | 10/2001 | Richter |
| 6,306,144 B1 | 10/2001 | Sydney et al. |
| 6,309,414 B1 | 10/2001 | Rolando et al. |
| 6,312,463 B1 | 11/2001 | Rourke et al. |
| 6,315,708 B1 | 11/2001 | Salmon et al. |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,312 B1 | 12/2001 | Lee et al. |
| 6,335,029 B1 | 1/2002 | Kamath et al. |
| 6,337,076 B1 | 1/2002 | Studin |
| 6,338,739 B1 | 1/2002 | Datta et al. |
| 6,342,507 B1 | 1/2002 | Naicker et al. |
| 6,344,055 B1 | 2/2002 | Shukov |
| 6,348,960 B1 | 2/2002 | Etori et al. |
| 6,358,276 B1 | 3/2002 | Edwin |
| 6,364,823 B1 | 4/2002 | Garibaldi et al. |
| 6,364,856 B1 | 4/2002 | Ding et al. |
| 6,364,903 B2 | 4/2002 | Tseng et al. |
| 6,366,808 B1 | 4/2002 | Schroeppel et al. |
| 6,368,658 B1 | 4/2002 | Schwarz et al. |
| 6,369,355 B1 | 4/2002 | Saunders |
| 6,375,826 B1 | 4/2002 | Wang et al. |
| 6,379,379 B1 | 4/2002 | Wang |
| 6,379,382 B1 | 4/2002 | Yang et al. |
| 6,379,383 B1 | 4/2002 | Palmaz et al. |
| 6,379,392 B1 | 4/2002 | Walak |
| 6,383,214 B1 | 5/2002 | Banas et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,033 B2 | 5/2002 | Ryan |
| 6,391,052 B2 | 5/2002 | Buirge et al. |
| 6,395,326 B1 | 5/2002 | Castro et al. |
| 6,398,806 B1 | 6/2002 | You |
| 6,409,754 B1 | 6/2002 | Smith et al. |
| 6,419,692 B1 | 7/2002 | Yang et al. |
| 6,423,092 B2 | 7/2002 | Datta et al. |
| 6,425,855 B2 | 7/2002 | Tomonto |
| 6,436,133 B1 | 8/2002 | Furst et al. |
| 6,440,166 B1 | 8/2002 | Kolluri |
| 6,440,487 B1 * | 8/2002 | Delfino et al. ............... 427/2.24 |
| 6,440,503 B1 | 8/2002 | Merdan et al. |
| 6,447,540 B1 | 9/2002 | Fontaine et al. |
| 6,451,871 B1 | 9/2002 | Winterton et al. |
| 6,458,153 B1 | 10/2002 | Bailey et al. |
| 6,468,304 B1 | 10/2002 | Dubois-Rande et al. |
| 6,471,721 B1 | 10/2002 | Dang |
| 6,471,980 B2 | 10/2002 | Sirhan et al. |

(56) References Cited

U.S. PATENT DOCUMENTS

| | | |
|---|---|---|
| 6,475,477 B1 | 11/2002 | Kohn et al. |
| 6,478,815 B1 | 11/2002 | Alt |
| 6,479,146 B1 | 11/2002 | Caruso et al. |
| 6,486,588 B2 | 11/2002 | Doron |
| 6,488,702 B1 | 12/2002 | Besselink |
| 6,491,666 B1 | 12/2002 | Santini, Jr. et al. |
| 6,491,720 B1 | 12/2002 | Vallana et al. |
| 6,492,096 B1 | 12/2002 | Liu et al. |
| 6,503,556 B2 | 1/2003 | Harish et al. |
| 6,503,921 B2 | 1/2003 | Naicker et al. |
| 6,506,437 B1 | 1/2003 | Harish et al. |
| 6,506,972 B1 | 1/2003 | Wang |
| 6,508,832 B1 | 1/2003 | Jalisi et al. |
| 6,514,283 B2 | 2/2003 | DiMatteo et al. |
| 6,517,571 B1 | 2/2003 | Brauker et al. |
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,529,774 B1 | 3/2003 | Greene |
| 6,530,949 B2 | 3/2003 | Konya et al. |
| 6,530,951 B1 | 3/2003 | Bates et al. |
| 6,533,905 B2 | 3/2003 | Johnson et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,549,811 B2 | 4/2003 | Stewart et al. |
| 6,554,854 B1 | 4/2003 | Flanagan |
| 6,555,157 B1 | 4/2003 | Hossainy et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,586,705 B1 | 7/2003 | Schell |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B1 | 9/2003 | Alt |
| 6,613,432 B2 | 9/2003 | Zamora et al. |
| 6,616,765 B1 | 9/2003 | Castro et al. |
| 6,626,933 B1 | 9/2003 | Lau et al. |
| 6,626,936 B2 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,696,666 B2 | 2/2004 | Merdan et al. |
| 6,696,667 B1 | 2/2004 | Flanagan |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Burrell et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B1 | 4/2004 | Kramer et al. |
| 6,726,712 B1 | 4/2004 | Raeder-Devens |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |

(56) References Cited

U.S. PATENT DOCUMENTS

| | | |
|---|---|---|
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,938,668 B2 | 9/2005 | Whitcher et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |
| 7,001,421 B2 | 2/2006 | Cheng et al. |
| 7,004,968 B2 | 2/2006 | Lootz et al. |
| 7,011,670 B2 | 3/2006 | Radisch, Jr. |
| 7,011,678 B2 | 3/2006 | Tenerz et al. |
| 7,011,680 B2 | 3/2006 | Alt |
| 7,018,408 B2 | 3/2006 | Bailey et al. |
| 7,022,334 B1 | 4/2006 | Ding et al. |
| 7,041,130 B2 | 5/2006 | Santini, Jr. |
| 7,048,767 B2 | 5/2006 | Namavar |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,060,051 B2 | 6/2006 | Palasis |
| 7,060,240 B2 | 6/2006 | Costa et al. |
| 7,063,748 B2 | 6/2006 | Talton |
| 7,067,606 B2 | 6/2006 | Mather et al. |
| 7,070,576 B2 | 7/2006 | O'Brien et al. |
| 7,077,859 B2 | 7/2006 | Sirhan et al. |
| 7,078,108 B2 | 7/2006 | Zhang et al. |
| 7,099,091 B2 | 8/2006 | Taniguchi et al. |
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,108,716 B2 | 9/2006 | Burnside et al. |
| 7,157,096 B2 | 1/2007 | Zhang et al. |
| 7,160,592 B2 | 1/2007 | Rypacek et al. |
| 7,163,715 B1 | 1/2007 | Kramer |
| 7,169,173 B2 | 1/2007 | Hossainy et al. |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |
| 7,208,172 B2 | 4/2007 | Birdsall et al. |
| 7,220,816 B2 | 5/2007 | Pacetti |
| 7,226,475 B2 | 6/2007 | Lenz et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,241,295 B2 | 7/2007 | Maguire |
| 7,244,272 B2 | 7/2007 | Dubson et al. |
| 7,261,732 B2 | 8/2007 | Justino |
| 7,261,734 B2 | 8/2007 | Gellman et al. |
| 7,261,735 B2 | 8/2007 | Llanos et al. |
| 7,267,960 B2 | 9/2007 | Galibert et al. |
| 7,279,174 B2 | 10/2007 | Pacetti |
| 7,279,175 B2 | 10/2007 | Chen |
| 7,294,409 B2 | 11/2007 | Lye et al. |
| 7,311,727 B2 | 12/2007 | Mazumder et al. |
| 7,323,189 B2 | 1/2008 | Pathak |
| RE40,122 E | 2/2008 | Thompson |
| 7,331,993 B2 | 2/2008 | White |
| 7,335,375 B2 | 2/2008 | Li et al. |
| 7,344,560 B2 | 3/2008 | Gregorich et al. |
| 7,344,563 B2 | 3/2008 | Vallana et al. |
| 7,393,589 B2 | 7/2008 | Aharonov et al. |
| 7,402,173 B2 | 7/2008 | Scheuermann et al. |
| 7,416,558 B2 | 8/2008 | Yip et al. |
| 7,432,327 B2 | 10/2008 | Glasgow et al. |
| 7,462,366 B2 | 12/2008 | Lanphere |
| 7,498,385 B2 | 3/2009 | Swetlin et al. |
| 7,507,433 B2 | 3/2009 | Weber |
| 7,537,610 B2 | 5/2009 | Reiss |
| 7,547,445 B2 | 6/2009 | Chudzik et al. |
| 7,563,277 B2 | 7/2009 | Case et al. |
| 7,637,941 B1 | 12/2009 | Manicka et al. |
| 7,651,527 B2 | 1/2010 | Krivoruchko et al. |
| 7,671,095 B2 | 3/2010 | Colson et al. |
| 7,691,401 B2 | 4/2010 | Castro et al. |
| 7,713,297 B2 | 5/2010 | Alt |
| 7,713,573 B2 | 5/2010 | Owens et al. |
| 7,722,805 B2 | 5/2010 | Hao et al. |
| 7,727,273 B2 | 6/2010 | Stinson et al. |
| 7,749,264 B2 | 7/2010 | Gregorich et al. |
| 7,758,635 B2 | 7/2010 | Parsonage |
| 7,771,773 B2 | 8/2010 | Namavar |
| 7,776,926 B1 | 8/2010 | Claude et al. |
| 7,906,147 B2 | 3/2011 | Hainfeld |
| 7,955,382 B2 | 6/2011 | Flanagan et al. |
| 7,981,150 B2 | 7/2011 | Scheuermann et al. |
| 7,985,252 B2 | 7/2011 | Radhakrishnan et al. |
| 7,988,192 B2 | 8/2011 | Numoto et al. |
| 7,998,192 B2 | 8/2011 | Atanasoska et al. |
| 8,133,278 B2 | 3/2012 | Atanasoska et al. |
| 8,158,728 B2 | 4/2012 | DeSimone et al. |
| 8,277,833 B2 | 10/2012 | Atanasoska et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0021871 A1 | 9/2001 | Stinson |
| 2001/0021873 A1 | 9/2001 | Stinson |
| 2001/0027299 A1 | 10/2001 | Yang et al. |
| 2001/0029398 A1 | 10/2001 | Jadhav |
| 2001/0029660 A1 | 10/2001 | Johnson |
| 2001/0032011 A1 | 10/2001 | Stanford |
| 2001/0032013 A1 | 10/2001 | Marton |
| 2001/0032014 A1 | 10/2001 | Yang et al. |
| 2001/0044650 A1 | 11/2001 | Simso et al. |
| 2002/0000175 A1 | 1/2002 | Hintermaier et al. |
| 2002/0000406 A1 | 1/2002 | Izumi |
| 2002/0004060 A1 | 1/2002 | Heublein et al. |
| 2002/0007102 A1 | 1/2002 | Salmon et al. |
| 2002/0007209 A1 | 1/2002 | Schearder et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0035394 A1 | 3/2002 | Fierens et al. |
| 2002/0038146 A1 | 3/2002 | Harry |
| 2002/0042039 A1 | 4/2002 | Kim et al. |
| 2002/0049495 A1 | 4/2002 | Kutryk et al. |
| 2002/0051730 A1 | 5/2002 | Bodnar et al. |
| 2002/0051846 A1 | 5/2002 | Kirkpatrick et al. |
| 2002/0065553 A1* | 5/2002 | Weber .................. 623/1.46 |
| 2002/0082680 A1 | 6/2002 | Sirhan et al. |
| 2002/0087123 A1 | 7/2002 | Hossainy et al. |
| 2002/0090313 A1 | 7/2002 | Wang et al. |
| 2002/0091375 A1 | 7/2002 | Sahatjian et al. |
| 2002/0098278 A1 | 7/2002 | Bates et al. |
| 2002/0099434 A1 | 7/2002 | Buscemi et al. |
| 2002/0099438 A1 | 7/2002 | Furst |
| 2002/0103527 A1 | 8/2002 | Kocur et al. |

(56) References Cited

U.S. PATENT DOCUMENTS

| | | |
|---|---|---|
| 2002/0103528 A1 | 8/2002 | Schaldach et al. |
| 2002/0111694 A1 | 8/2002 | Ellingsen et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133224 A1 | 9/2002 | Bajgar et al. |
| 2002/0138100 A1 | 9/2002 | Stoll et al. |
| 2002/0138131 A1 | 9/2002 | Solovay et al. |
| 2002/0138136 A1 | 9/2002 | Chandresekaran et al. |
| 2002/0138154 A1 | 9/2002 | Li et al. |
| 2002/0144757 A1 | 10/2002 | Craig et al. |
| 2002/0151964 A1 | 10/2002 | Smith et al. |
| 2002/0155212 A1 | 10/2002 | Hossainy |
| 2002/0165265 A1 | 11/2002 | Hunter et al. |
| 2002/0165578 A1 | 11/2002 | Sawitowski et al. |
| 2002/0165600 A1 | 11/2002 | Banas et al. |
| 2002/0165607 A1 | 11/2002 | Alt |
| 2002/0169493 A1 | 11/2002 | Widenhouse et al. |
| 2002/0177042 A1 | 11/2002 | Amendola |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0187260 A1 | 12/2002 | Sheppard, Jr. et al. |
| 2002/0193336 A1 | 12/2002 | Elkins et al. |
| 2002/0193682 A1 | 12/2002 | Torchia et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003127 A1 | 1/2003 | Brown et al. |
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0009214 A1 | 1/2003 | Shanley |
| 2003/0018380 A1 | 1/2003 | Craig et al. |
| 2003/0018381 A1 | 1/2003 | Whitcher et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0044596 A1 | 3/2003 | Lazarov et al. |
| 2003/0050687 A1 | 3/2003 | Schwade et al. |
| 2003/0050692 A1 | 3/2003 | Sirhan et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0064095 A1 | 4/2003 | Martin et al. |
| 2003/0068355 A1 | 4/2003 | Shanley et al. |
| 2003/0069631 A1 | 4/2003 | Stoll |
| 2003/0074053 A1 | 4/2003 | Palmaz et al. |
| 2003/0077200 A1 | 4/2003 | Craig et al. |
| 2003/0077310 A1 | 4/2003 | Pathak et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1 | 5/2003 | Shulze et al. |
| 2003/0088312 A1 | 5/2003 | Kopia et al. |
| 2003/0099684 A1 | 5/2003 | Domb |
| 2003/0100815 A1 | 5/2003 | Da Silva et al. |
| 2003/0100830 A1 | 5/2003 | Zhong et al. |
| 2003/0104030 A1 | 6/2003 | Igaki et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118692 A1 | 6/2003 | Wang et al. |
| 2003/0120339 A1 | 6/2003 | Banik et al. |
| 2003/0124055 A1 | 7/2003 | Li et al. |
| 2003/0125803 A1 | 7/2003 | Vallana |
| 2003/0130718 A1 | 7/2003 | Palmas et al. |
| 2003/0139799 A1 | 7/2003 | Ley et al. |
| 2003/0143330 A1 | 7/2003 | Loomis et al. |
| 2003/0144728 A1 | 7/2003 | Scheuermann et al. |
| 2003/0150380 A1 | 8/2003 | Yoe |
| 2003/0153901 A1 | 8/2003 | Herweck et al. |
| 2003/0153971 A1 | 8/2003 | Chandrasekaran |
| 2003/0158598 A1 | 8/2003 | Ashton et al. |
| 2003/0170605 A1 | 9/2003 | Long et al. |
| 2003/0181973 A1 | 9/2003 | Sahota |
| 2003/0181975 A1 | 9/2003 | Ishii et al. |
| 2003/0185895 A1 | 10/2003 | Lanphere |
| 2003/0190406 A1 | 10/2003 | Hossainy et al. |
| 2003/0195613 A1 | 10/2003 | Curcio et al. |
| 2003/0199993 A1 | 10/2003 | Gellman et al. |
| 2003/0204239 A1 | 10/2003 | Carlyle et al. |
| 2003/0211135 A1 | 11/2003 | Greenhalgh et al. |
| 2003/0216803 A1 | 11/2003 | Ledergerber |
| 2003/0219562 A1 | 11/2003 | Rypacek et al. |
| 2003/0221307 A1 | 12/2003 | Kaese et al. |
| 2003/0228523 A1 | 12/2003 | DeLongchamp et al. |
| 2003/0236513 A1 | 12/2003 | Schwarz et al. |
| 2004/0000046 A1* | 1/2004 | Stinson ................. 29/426.4 |
| 2004/0000540 A1 | 1/2004 | Soboyejo et al. |
| 2004/0004063 A1 | 1/2004 | Merdan |
| 2004/0006382 A1 | 1/2004 | Sohier |
| 2004/0018296 A1 | 1/2004 | Castro et al. |
| 2004/0019376 A1 | 1/2004 | Alt |
| 2004/0022939 A1 | 2/2004 | Kim et al. |
| 2004/0024448 A1 | 2/2004 | Chang et al. |
| 2004/0029303 A1 | 2/2004 | Hart et al. |
| 2004/0030218 A1 | 2/2004 | Kocur et al. |
| 2004/0030377 A1 | 2/2004 | Dubson et al. |
| 2004/0030379 A1 | 2/2004 | Hamm et al. |
| 2004/0034409 A1 | 2/2004 | Heublein et al. |
| 2004/0039438 A1 | 2/2004 | Alt |
| 2004/0039441 A1 | 2/2004 | Rowland et al. |
| 2004/0044397 A1 | 3/2004 | Stinson |
| 2004/0047980 A1 | 3/2004 | Pacetti et al. |
| 2004/0059407 A1 | 3/2004 | Escamilla et al. |
| 2004/0059409 A1 | 3/2004 | Stenzel |
| 2004/0067301 A1 | 4/2004 | Ding |
| 2004/0071861 A1 | 4/2004 | Mandrusov et al. |
| 2004/0073155 A1 | 4/2004 | Laufer et al. |
| 2004/0073284 A1 | 4/2004 | Bates et al. |
| 2004/0073293 A1 | 4/2004 | Thompson |
| 2004/0073297 A1 | 4/2004 | Rohde et al. |
| 2004/0073298 A1 | 4/2004 | Hossainy |
| 2004/0078071 A1 | 4/2004 | Escamilla et al. |
| 2004/0082682 A1 | 4/2004 | Loomis et al. |
| 2004/0088038 A1 | 5/2004 | Dehnad et al. |
| 2004/0088041 A1 | 5/2004 | Stanford |
| 2004/0093071 A1 | 5/2004 | Jang |
| 2004/0093075 A1 | 5/2004 | Kuehne |
| 2004/0093076 A1 | 5/2004 | White et al. |
| 2004/0098089 A1 | 5/2004 | Weber |
| 2004/0098090 A1* | 5/2004 | Williams et al. ............. 623/1.13 |
| 2004/0098108 A1 | 5/2004 | Harder et al. |
| 2004/0098119 A1 | 5/2004 | Wang |
| 2004/0106975 A1 | 6/2004 | Solovay et al. |
| 2004/0106984 A1 | 6/2004 | Stinson |
| 2004/0106985 A1 | 6/2004 | Jang |
| 2004/0111150 A1 | 6/2004 | Berg et al. |
| 2004/0116999 A1 | 6/2004 | Ledergerber |
| 2004/0117005 A1 | 6/2004 | Gadde et al. |
| 2004/0117008 A1 | 6/2004 | Wnendt et al. |
| 2004/0122504 A1 | 6/2004 | Hogendijk |
| 2004/0126566 A1 | 7/2004 | Axen et al. |
| 2004/0133270 A1 | 7/2004 | Grandt |
| 2004/0134886 A1 | 7/2004 | Wagner et al. |
| 2004/0137039 A1 | 7/2004 | Sukhishvili et al. |
| 2004/0138738 A1 | 7/2004 | Stinson |
| 2004/0142014 A1 | 7/2004 | Litvack et al. |
| 2004/0143317 A1 | 7/2004 | Stinson et al. |
| 2004/0143321 A1 | 7/2004 | Litvack et al. |
| 2004/0148010 A1 | 7/2004 | Rush |
| 2004/0148015 A1 | 7/2004 | Lye et al. |
| 2004/0153138 A1 | 8/2004 | Murphy |
| 2004/0157073 A1 | 8/2004 | Burrell et al. |
| 2004/0158308 A1 | 8/2004 | Hogendijk et al. |
| 2004/0158310 A1 | 8/2004 | Weber et al. |
| 2004/0167572 A1 | 8/2004 | Roth et al. |
| 2004/0167609 A1 | 8/2004 | Majercak |

(56) References Cited

U.S. PATENT DOCUMENTS

| | | |
|---|---|---|
| 2004/0167612 A1 | 8/2004 | Grignani et al. |
| 2004/0172124 A1 | 9/2004 | Vallana et al. |
| 2004/0181252 A1 | 9/2004 | Boyle et al. |
| 2004/0181275 A1 | 9/2004 | Noble et al. |
| 2004/0181276 A1 | 9/2004 | Brown et al. |
| 2004/0181278 A1 | 9/2004 | Tseng et al. |
| 2004/0182511 A1 | 9/2004 | Rakos et al. |
| 2004/0186553 A1 | 9/2004 | Yan |
| 2004/0191293 A1 | 9/2004 | Claude |
| 2004/0191404 A1 | 9/2004 | Hossainy et al. |
| 2004/0202692 A1 | 10/2004 | Shanley et al. |
| 2004/0204750 A1 | 10/2004 | Dinh |
| 2004/0211362 A1 | 10/2004 | Castro et al. |
| 2004/0219214 A1 | 11/2004 | Gravett et al. |
| 2004/0220510 A1 | 11/2004 | Koullick et al. |
| 2004/0220659 A1 | 11/2004 | Girton |
| 2004/0220660 A1 | 11/2004 | Shanley et al. |
| 2004/0220662 A1 | 11/2004 | Dang et al. |
| 2004/0224001 A1 | 11/2004 | Pacetti et al. |
| 2004/0225346 A1 | 11/2004 | Mazumder et al. |
| 2004/0228905 A1 | 11/2004 | Greenspan et al. |
| 2004/0230176 A1 | 11/2004 | Shanahan et al. |
| 2004/0230225 A1 | 11/2004 | Penner et al. |
| 2004/0230290 A1 | 11/2004 | Weber et al. |
| 2004/0230293 A1 | 11/2004 | Yip et al. |
| 2004/0234737 A1 | 11/2004 | Pacetti |
| 2004/0236415 A1 | 11/2004 | Thomas |
| 2004/0236416 A1 | 11/2004 | Falotico |
| 2004/0237282 A1 | 12/2004 | Hines |
| 2004/0242106 A1 | 12/2004 | Rabasco et al. |
| 2004/0243217 A1 | 12/2004 | Andersen |
| 2004/0243237 A1 | 12/2004 | Unwin et al. |
| 2004/0243241 A1 | 12/2004 | Istephanous et al. |
| 2004/0247671 A1 | 12/2004 | Prescott et al. |
| 2004/0249440 A1 | 12/2004 | Bucker et al. |
| 2004/0249443 A1 | 12/2004 | Shanley et al. |
| 2004/0249444 A1 | 12/2004 | Reiss |
| 2004/0249445 A1 | 12/2004 | Rosenthal et al. |
| 2004/0249449 A1 | 12/2004 | Shanley et al. |
| 2004/0254419 A1 | 12/2004 | Wang et al. |
| 2004/0254635 A1 | 12/2004 | Shanley et al. |
| 2005/0004661 A1 | 1/2005 | Lewis et al. |
| 2005/0010275 A1 | 1/2005 | Sahatjian |
| 2005/0010279 A1 | 1/2005 | Tenerz et al. |
| 2005/0015142 A1 | 1/2005 | Austin et al. |
| 2005/0019265 A1 | 1/2005 | Hammer et al. |
| 2005/0019371 A1 | 1/2005 | Anderson et al. |
| 2005/0021127 A1 | 1/2005 | Kawula |
| 2005/0021128 A1 | 1/2005 | Nakahama et al. |
| 2005/0022627 A1 | 2/2005 | Chen |
| 2005/0025804 A1 | 2/2005 | Heller |
| 2005/0027350 A1 | 2/2005 | Momma et al. |
| 2005/0033407 A1 | 2/2005 | Weber et al. |
| 2005/0033411 A1 | 2/2005 | Wu et al. |
| 2005/0033412 A1 | 2/2005 | Wu et al. |
| 2005/0033417 A1 | 2/2005 | Borges et al. |
| 2005/0037047 A1 | 2/2005 | Song |
| 2005/0037050 A1 | 2/2005 | Weber |
| 2005/0038134 A1 | 2/2005 | Loomis et al. |
| 2005/0038501 A1 | 2/2005 | Moore, Jr. et al. |
| 2005/0042288 A1 | 2/2005 | Koblish et al. |
| 2005/0042440 A1 | 2/2005 | Bach et al. |
| 2005/0055044 A1 | 3/2005 | Kangas |
| 2005/0055080 A1 | 3/2005 | Istephanous et al. |
| 2005/0055085 A1 | 3/2005 | Rivron et al. |
| 2005/0060020 A1 | 3/2005 | Jenson |
| 2005/0060021 A1 | 3/2005 | O'Brien et al. |
| 2005/0064088 A1 | 3/2005 | Fredrickson |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0070996 A1 | 3/2005 | Dinh et al. |
| 2005/0071016 A1 | 3/2005 | Hausdorf et al. |
| 2005/0072544 A1 | 4/2005 | Palmaz et al. |
| 2005/0074479 A1 | 4/2005 | Weber et al. |
| 2005/0074545 A1 | 4/2005 | Thomas |
| 2005/0075714 A1 | 4/2005 | Cheng et al. |
| 2005/0077305 A1 | 4/2005 | Guevara |
| 2005/0079132 A1 | 4/2005 | Wang et al. |
| 2005/0079199 A1 | 4/2005 | Heruth et al. |
| 2005/0079356 A1 | 4/2005 | Rathenow et al. |
| 2005/0092615 A1 | 5/2005 | Birdsall et al. |
| 2005/0096731 A1 | 5/2005 | Looi et al. |
| 2005/0100577 A1 | 5/2005 | Parker et al. |
| 2005/0100609 A1 | 5/2005 | Claude |
| 2005/0102025 A1 | 5/2005 | Laroche et al. |
| 2005/0106212 A1 | 5/2005 | Gertner et al. |
| 2005/0107869 A1 | 5/2005 | Sirhan et al. |
| 2005/0107870 A1 | 5/2005 | Wang et al. |
| 2005/0113936 A1 | 5/2005 | Brustad et al. |
| 2005/0119723 A1 | 6/2005 | Peacock |
| 2005/0119725 A1 | 6/2005 | Wang et al. |
| 2005/0129727 A1 | 6/2005 | Weber et al. |
| 2005/0129731 A1 | 6/2005 | Horres et al. |
| 2005/0131509 A1 | 6/2005 | Atanassoska et al. |
| 2005/0131521 A1 | 6/2005 | Marton |
| 2005/0131522 A1 | 6/2005 | Stinson et al. |
| 2005/0131527 A1 | 6/2005 | Pathak |
| 2005/0131528 A1 | 6/2005 | Buscemi et al. |
| 2005/0136090 A1 | 6/2005 | Falotico et al. |
| 2005/0137677 A1 | 6/2005 | Rush |
| 2005/0137679 A1 | 6/2005 | Changelian et al. |
| 2005/0137684 A1 | 6/2005 | Changelian et al. |
| 2005/0149169 A1 | 7/2005 | Wang et al. |
| 2005/0149170 A1 | 7/2005 | Tassel et al. |
| 2005/0149175 A1 | 7/2005 | Hunter et al. |
| 2005/0149177 A1 | 7/2005 | Weber et al. |
| 2005/0159804 A1 | 7/2005 | Lad et al. |
| 2005/0159805 A1 | 7/2005 | Weber et al. |
| 2005/0159809 A1 | 7/2005 | Hezi-Yamit et al. |
| 2005/0160600 A1 | 7/2005 | Bien et al. |
| 2005/0163821 A1 | 7/2005 | Sung et al. |
| 2005/0163954 A1 | 7/2005 | Shaw |
| 2005/0165301 A1 | 7/2005 | Smith et al. |
| 2005/0165468 A1 | 7/2005 | Marton |
| 2005/0165470 A1 | 7/2005 | Weber |
| 2005/0169969 A1 | 8/2005 | Li et al. |
| 2005/0171595 A1 | 8/2005 | Feldman et al. |
| 2005/0177226 A1 | 8/2005 | Banik et al. |
| 2005/0180919 A1 | 8/2005 | Tedeschi |
| 2005/0182361 A1 | 8/2005 | Lennox |
| 2005/0182478 A1 | 8/2005 | Holman et al. |
| 2005/0186250 A1 | 8/2005 | Gertner et al. |
| 2005/0187605 A1 | 8/2005 | Greenhalgh et al. |
| 2005/0187611 A1 | 8/2005 | Ding et al. |
| 2005/0187615 A1 | 8/2005 | Williams et al. |
| 2005/0192657 A1 | 9/2005 | Colen et al. |
| 2005/0192662 A1 | 9/2005 | Ward |
| 2005/0192664 A1 | 9/2005 | Eisert |
| 2005/0196424 A1 | 9/2005 | Chappa |
| 2005/0208098 A1 | 9/2005 | Castro et al. |
| 2005/0208100 A1 | 9/2005 | Weber et al. |
| 2005/0209680 A1 | 9/2005 | Gale et al. |
| 2005/0209681 A1 | 9/2005 | Curcio et al. |
| 2005/0211680 A1 | 9/2005 | Li et al. |
| 2005/0214951 A1 | 9/2005 | Nahm et al. |
| 2005/0216074 A1 | 9/2005 | Sahatjian |
| 2005/0216075 A1 | 9/2005 | Wang et al. |
| 2005/0220853 A1 | 10/2005 | Dao et al. |
| 2005/0221072 A1 | 10/2005 | Dubrow et al. |
| 2005/0222671 A1 | 10/2005 | Schaeffer et al. |
| 2005/0228477 A1 | 10/2005 | Grainger et al. |
| 2005/0228483 A1 | 10/2005 | Kaplan et al. |
| 2005/0228491 A1 | 10/2005 | Snyder et al. |
| 2005/0232968 A1 | 10/2005 | Palmaz et al. |
| 2005/0233965 A1 | 10/2005 | Schwartz et al. |
| 2005/0234538 A1 | 10/2005 | Litvack et al. |
| 2005/0240100 A1 | 10/2005 | Wang et al. |
| 2005/0240280 A1 | 10/2005 | Aliski et al. |
| 2005/0244459 A1 | 11/2005 | DeWitt et al. |
| 2005/0251245 A1 | 11/2005 | Sieradzki et al. |
| 2005/0251249 A1 | 11/2005 | Sahatjian |
| 2005/0252893 A1 | 11/2005 | Shapovalov et al. |
| 2005/0255707 A1 | 11/2005 | Hart et al. |

(56) References Cited

U.S. PATENT DOCUMENTS

| | | |
|---|---|---|
| 2005/0261760 A1 | 11/2005 | Weber |
| 2005/0266039 A1 | 12/2005 | Weber |
| 2005/0266040 A1 | 12/2005 | Gerberding |
| 2005/0266041 A1 | 12/2005 | Gerold et al. |
| 2005/0267560 A1 | 12/2005 | Bates et al. |
| 2005/0267561 A1 | 12/2005 | Jones et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0278016 A1 | 12/2005 | Welsh et al. |
| 2005/0278021 A1 | 12/2005 | Bates et al. |
| 2005/0281863 A1 | 12/2005 | Anderson et al. |
| 2005/0283224 A1 | 12/2005 | King |
| 2005/0283229 A1 | 12/2005 | Dugan et al. |
| 2005/0287188 A1 | 12/2005 | Anderson et al. |
| 2005/0288481 A1 | 12/2005 | DesNoyer et al. |
| 2006/0002979 A1 | 1/2006 | Ashammakhi et al. |
| 2006/0009839 A1 | 1/2006 | Tan |
| 2006/0013850 A1 | 1/2006 | Domb |
| 2006/0014039 A1 | 1/2006 | Zhang et al. |
| 2006/0015175 A1 | 1/2006 | Palmaz et al. |
| 2006/0015361 A1 | 1/2006 | Sattler et al. |
| 2006/0020742 A1 | 1/2006 | Au et al. |
| 2006/0025848 A1 | 2/2006 | Weber et al. |
| 2006/0035026 A1 | 2/2006 | Atanassoska et al. |
| 2006/0036281 A1 | 2/2006 | Patterson et al. |
| 2006/0036311 A1 | 2/2006 | Nakayama et al. |
| 2006/0038027 A1 | 2/2006 | O'Connor et al. |
| 2006/0040388 A1 | 2/2006 | Bromberg et al. |
| 2006/0041182 A1 | 2/2006 | Forbes et al. |
| 2006/0051397 A1 | 3/2006 | Maier et al. |
| 2006/0052744 A1 | 3/2006 | Weber |
| 2006/0052863 A1 | 3/2006 | Harder et al. |
| 2006/0052864 A1 | 3/2006 | Harder et al. |
| 2006/0058868 A1 | 3/2006 | Gale et al. |
| 2006/0062820 A1 | 3/2006 | Gertner et al. |
| 2006/0064160 A1 | 3/2006 | Gerold et al. |
| 2006/0067908 A1 | 3/2006 | Ding |
| 2006/0069427 A1 | 3/2006 | Savage et al. |
| 2006/0074480 A1 | 4/2006 | Bales et al. |
| 2006/0075044 A1 | 4/2006 | Fox et al. |
| 2006/0075092 A1 | 4/2006 | Kidokoro |
| 2006/0079958 A1 | 4/2006 | Stratford et al. |
| 2006/0085062 A1 | 4/2006 | Lee et al. |
| 2006/0085065 A1 | 4/2006 | Krause et al. |
| 2006/0088566 A1 | 4/2006 | Parsonage et al. |
| 2006/0088567 A1 | 4/2006 | Warner et al. |
| 2006/0088653 A1 | 4/2006 | Chappa et al. |
| 2006/0088666 A1 | 4/2006 | Kobrin et al. |
| 2006/0100696 A1 | 5/2006 | Atanasoska et al. |
| 2006/0115512 A1 | 6/2006 | Peacock et al. |
| 2006/0118236 A1 | 6/2006 | House et al. |
| 2006/0121080 A1 | 6/2006 | Lye et al. |
| 2006/0122694 A1 | 6/2006 | Stinson et al. |
| 2006/0122697 A1 | 6/2006 | Shanley et al. |
| 2006/0124472 A1* | 6/2006 | Rokicki .................. 205/640 |
| 2006/0127266 A1 | 6/2006 | Miura et al. |
| 2006/0129215 A1 | 6/2006 | Helmus et al. |
| 2006/0129222 A1 | 6/2006 | Stinson |
| 2006/0129225 A1 | 6/2006 | Kopia et al. |
| 2006/0136048 A1 | 6/2006 | Pacetti et al. |
| 2006/0136051 A1 | 6/2006 | Furst et al. |
| 2006/0141156 A1 | 6/2006 | Viel et al. |
| 2006/0149352 A1 | 7/2006 | Schlun |
| 2006/0153729 A1 | 7/2006 | Stinson et al. |
| 2006/0155361 A1 | 7/2006 | Schomig et al. |
| 2006/0167543 A1 | 7/2006 | Bailey et al. |
| 2006/0177480 A1 | 8/2006 | Sung et al. |
| 2006/0178727 A1 | 8/2006 | Richter |
| 2006/0184235 A1 | 8/2006 | Rivron et al. |
| 2006/0193886 A1 | 8/2006 | Owens et al. |
| 2006/0193887 A1 | 8/2006 | Owens et al. |
| 2006/0193888 A1 | 8/2006 | Lye et al. |
| 2006/0193889 A1 | 8/2006 | Spradlin et al. |
| 2006/0193890 A1 | 8/2006 | Owens et al. |
| 2006/0193892 A1 | 8/2006 | Furst et al. |
| 2006/0195142 A1 | 8/2006 | Shalaby |
| 2006/0198869 A1 | 9/2006 | Furst et al. |
| 2006/0199876 A1 | 9/2006 | Troczynski et al. |
| 2006/0200229 A1 | 9/2006 | Burgermeister et al. |
| 2006/0200231 A1 | 9/2006 | O'Brien et al. |
| 2006/0200232 A1 | 9/2006 | Phaneuf et al. |
| 2006/0200233 A1 | 9/2006 | Kujawski |
| 2006/0204441 A1 | 9/2006 | Atala et al. |
| 2006/0204445 A1 | 9/2006 | Atala et al. |
| 2006/0210595 A1 | 9/2006 | Singhvi et al. |
| 2006/0212108 A1 | 9/2006 | Tittelbach |
| 2006/0222679 A1 | 10/2006 | Shanley et al. |
| 2006/0222844 A1 | 10/2006 | Stinson |
| 2006/0224237 A1 | 10/2006 | Furst et al. |
| 2006/0229711 A1 | 10/2006 | Yan et al. |
| 2006/0229713 A1 | 10/2006 | Shanley et al. |
| 2006/0230476 A1 | 10/2006 | Atanasoska et al. |
| 2006/0233941 A1 | 10/2006 | Olson |
| 2006/0241739 A1 | 10/2006 | Besselink et al. |
| 2006/0251701 A1 | 11/2006 | Lynn et al. |
| 2006/0259133 A1 | 11/2006 | Sowinski et al. |
| 2006/0264138 A1 | 11/2006 | Sowinski et al. |
| 2006/0271156 A1 | 11/2006 | Ledergerber |
| 2006/0271168 A1 | 11/2006 | Kleine et al. |
| 2006/0271169 A1 | 11/2006 | Lye et al. |
| 2006/0271192 A1 | 11/2006 | Olsen et al. |
| 2006/0275554 A1 | 12/2006 | Zhao et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0276884 A1 | 12/2006 | Lye et al. |
| 2006/0276885 A1 | 12/2006 | Lye et al. |
| 2006/0280770 A1 | 12/2006 | Hossainy et al. |
| 2006/0287709 A1 | 12/2006 | Rao |
| 2006/0287710 A1 | 12/2006 | Lendlein et al. |
| 2006/0292388 A1 | 12/2006 | Palumbo et al. |
| 2007/0003589 A1 | 1/2007 | Astafieva et al. |
| 2007/0003596 A1 | 1/2007 | Tittelbach et al. |
| 2007/0020306 A1 | 1/2007 | Schultheiss |
| 2007/0027532 A1 | 2/2007 | Wang et al. |
| 2007/0032858 A1 | 2/2007 | Santos et al. |
| 2007/0032862 A1 | 2/2007 | Weber et al. |
| 2007/0032864 A1 | 2/2007 | Furst et al. |
| 2007/0034615 A1 | 2/2007 | Kleine |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0038290 A1 | 2/2007 | Huang et al. |
| 2007/0045252 A1 | 3/2007 | Kleine et al. |
| 2007/0048350 A1 | 3/2007 | Faltico et al. |
| 2007/0050007 A1 | 3/2007 | Kondyurin et al. |
| 2007/0050009 A1 | 3/2007 | Flanagan |
| 2007/0052497 A1 | 3/2007 | Tada |
| 2007/0055349 A1 | 3/2007 | Santos et al. |
| 2007/0055354 A1 | 3/2007 | Santos et al. |
| 2007/0055364 A1* | 3/2007 | Hossainy et al. ............ 623/1.38 |
| 2007/0059435 A1 | 3/2007 | Santos et al. |
| 2007/0065418 A1 | 3/2007 | Vallana et al. |
| 2007/0073385 A1 | 3/2007 | Schaeffer et al. |
| 2007/0073390 A1 | 3/2007 | Lee |
| 2007/0077163 A1 | 4/2007 | Furst et al. |
| 2007/0100385 A1 | 5/2007 | Rawat et al. |
| 2007/0104753 A1 | 5/2007 | Flanagan |
| 2007/0106347 A1 | 5/2007 | Lin |
| 2007/0106363 A1 | 5/2007 | Weber |
| 2007/0123131 A1 | 5/2007 | Nguyen et al. |
| 2007/0123973 A1 | 5/2007 | Roth et al. |
| 2007/0125247 A1 | 6/2007 | Kunstmann et al. |
| 2007/0129789 A1 | 6/2007 | Cottone, Jr. et al. |
| 2007/0129792 A1 | 6/2007 | Picart et al. |
| 2007/0134288 A1 | 6/2007 | Parsonage et al. |
| 2007/0135908 A1* | 6/2007 | Zhao ........................... 623/1.46 |
| 2007/0141106 A1 | 6/2007 | Bonutti et al. |
| 2007/0142897 A1 | 6/2007 | Consigny et al. |
| 2007/0142899 A1 | 6/2007 | Lootz et al. |
| 2007/0148251 A1 | 6/2007 | Hossainy et al. |
| 2007/0151093 A1 | 7/2007 | Curcio et al. |
| 2007/0156231 A1 | 7/2007 | Weber |

(56) References Cited

U.S. PATENT DOCUMENTS

| | | |
|---|---|---|
| 2007/0156248 A1 | 7/2007 | Marco et al. |
| 2007/0160641 A1 | 7/2007 | Jang |
| 2007/0168016 A1 | 7/2007 | Gronemeyer et al. |
| 2007/0173923 A1 | 7/2007 | Savage et al. |
| 2007/0178129 A1 | 8/2007 | Flanagan |
| 2007/0181433 A1 | 8/2007 | Birdsall et al. |
| 2007/0184083 A1 | 8/2007 | Coughlin |
| 2007/0190104 A1 | 8/2007 | Kamath et al. |
| 2007/0191923 A1 | 8/2007 | Weber |
| 2007/0191928 A1 | 8/2007 | Rolando et al. |
| 2007/0191931 A1 | 8/2007 | Weber |
| 2007/0191943 A1 | 8/2007 | Shrivastava et al. |
| 2007/0197980 A1 | 8/2007 | Barry et al. |
| 2007/0202466 A1 | 8/2007 | Schwarz et al. |
| 2007/0207186 A1 | 9/2007 | Scanlon et al. |
| 2007/0208412 A1 | 9/2007 | Elmaleh |
| 2007/0212388 A1 | 9/2007 | Patravale et al. |
| 2007/0219626 A1 | 9/2007 | Rolando et al. |
| 2007/0224116 A1 | 9/2007 | Chandrasekaran et al. |
| 2007/0224244 A1 | 9/2007 | Weber et al. |
| 2007/0225799 A1 | 9/2007 | Doty |
| 2007/0244541 A1 | 10/2007 | Schulman |
| 2007/0244569 A1 | 10/2007 | Weber et al. |
| 2007/0250155 A1 | 10/2007 | Simpson |
| 2007/0250156 A1 | 10/2007 | Palmaz |
| 2007/0250158 A1 | 10/2007 | Krivoruchko et al. |
| 2007/0255388 A1 | 11/2007 | Rudakov et al. |
| 2007/0255392 A1 | 11/2007 | Johnson |
| 2007/0264199 A1 | 11/2007 | Labhasetwar et al. |
| 2007/0264303 A1 | 11/2007 | Atanasoska et al. |
| 2007/0270940 A1 | 11/2007 | Doty |
| 2007/0270942 A1 | 11/2007 | Thomas |
| 2007/0281073 A1 | 12/2007 | Gale et al. |
| 2007/0281117 A1 | 12/2007 | Kaplan et al. |
| 2007/0282247 A1 | 12/2007 | Desai et al. |
| 2007/0282426 A1 | 12/2007 | Wang et al. |
| 2007/0282432 A1 | 12/2007 | Stinson et al. |
| 2007/0299509 A1 | 12/2007 | Ding |
| 2007/0299512 A1 | 12/2007 | Korzuschnik et al. |
| 2008/0003251 A1 | 1/2008 | Zhou |
| 2008/0003256 A1 | 1/2008 | Martens et al. |
| 2008/0003431 A1 | 1/2008 | Fellinger et al. |
| 2008/0004691 A1 | 1/2008 | Weber et al. |
| 2008/0031765 A1 | 2/2008 | Gerold et al. |
| 2008/0033522 A1 | 2/2008 | Grewe et al. |
| 2008/0033530 A1 | 2/2008 | Zberg et al. |
| 2008/0033531 A1 | 2/2008 | Barthel et al. |
| 2008/0033533 A1 | 2/2008 | Borck |
| 2008/0033536 A1 | 2/2008 | Wittchow |
| 2008/0033537 A1 | 2/2008 | Tittelbach |
| 2008/0033538 A1 | 2/2008 | Borck et al. |
| 2008/0033539 A1 | 2/2008 | Sternberg et al. |
| 2008/0033576 A1 | 2/2008 | Gerold et al. |
| 2008/0038146 A1 | 2/2008 | Wachter et al. |
| 2008/0050413 A1 | 2/2008 | Horvers et al. |
| 2008/0051335 A1 | 2/2008 | Kleiner et al. |
| 2008/0051866 A1 | 2/2008 | Chen et al. |
| 2008/0051872 A1 | 2/2008 | Borck |
| 2008/0051881 A1 | 2/2008 | Feng et al. |
| 2008/0057105 A1 | 3/2008 | Atanasoska et al. |
| 2008/0058919 A1 | 3/2008 | Kramer-Brown et al. |
| 2008/0058921 A1 | 3/2008 | Lindquist |
| 2008/0058923 A1 | 3/2008 | Bertsch et al. |
| 2008/0069854 A1 | 3/2008 | Xiao et al. |
| 2008/0069858 A1 | 3/2008 | Weber |
| 2008/0071348 A1 | 3/2008 | Boismier et al. |
| 2008/0071349 A1 | 3/2008 | Atanasoska et al. |
| 2008/0071350 A1 | 3/2008 | Stinson |
| 2008/0071351 A1 | 3/2008 | Flanagan et al. |
| 2008/0071352 A1 | 3/2008 | Weber et al. |
| 2008/0071353 A1 | 3/2008 | Weber et al. |
| 2008/0071355 A1 | 3/2008 | Weber et al. |
| 2008/0071357 A1 | 3/2008 | Girton et al. |
| 2008/0071358 A1 | 3/2008 | Weber et al. |
| 2008/0082162 A1 | 4/2008 | Boismier et al. |
| 2008/0086199 A1 | 4/2008 | Dave et al. |
| 2008/0086201 A1 | 4/2008 | Weber et al. |
| 2008/0090097 A1 | 4/2008 | Shaw et al. |
| 2008/0097577 A1 | 4/2008 | Atanasoska et al. |
| 2008/0103589 A1 | 5/2008 | Cheng et al. |
| 2008/0103594 A1 | 5/2008 | Loffler et al. |
| 2008/0107890 A1 | 5/2008 | Bureau et al. |
| 2008/0109072 A1 | 5/2008 | Girton |
| 2008/0113083 A1 | 5/2008 | Sutermeister et al. |
| 2008/0124373 A1 | 5/2008 | Xiao et al. |
| 2008/0131479 A1 | 6/2008 | Weber et al. |
| 2008/0140172 A1 | 6/2008 | Carpenter et al. |
| 2008/0140186 A1 | 6/2008 | Grignani et al. |
| 2008/0145400 A1 | 6/2008 | Weber et al. |
| 2008/0147175 A1 | 6/2008 | Krivoruchko et al. |
| 2008/0147177 A1 | 6/2008 | Scheuermann et al. |
| 2008/0148002 A1 | 6/2008 | Fleming |
| 2008/0152929 A1 | 6/2008 | Zhao |
| 2008/0160166 A1 | 7/2008 | Rypacek et al. |
| 2008/0160259 A1 | 7/2008 | Nielson et al. |
| 2008/0161906 A1 | 7/2008 | Atanasoska et al. |
| 2008/0171929 A1 | 7/2008 | Katims |
| 2008/0175885 A1 | 7/2008 | Asgari |
| 2008/0177378 A1 | 7/2008 | Asgari |
| 2008/0183269 A2 | 7/2008 | Kaplan et al. |
| 2008/0183277 A1 | 7/2008 | Atanasoska et al. |
| 2008/0183278 A1 | 7/2008 | Atanasoska et al. |
| 2008/0188927 A1 | 8/2008 | Rohde et al. |
| 2008/0195170 A1 | 8/2008 | Asgari |
| 2008/0195189 A1 | 8/2008 | Asgari |
| 2008/0195198 A1 | 8/2008 | Asgari |
| 2008/0208308 A1 | 8/2008 | Allen et al. |
| 2008/0208313 A1 | 8/2008 | Yu et al. |
| 2008/0208352 A1 | 8/2008 | Krivoruchko et al. |
| 2008/0213377 A1 | 9/2008 | Bhatia et al. |
| 2008/0215129 A1 | 9/2008 | Venturelli et al. |
| 2008/0215139 A1 | 9/2008 | McMorrow et al. |
| 2008/0215140 A1 | 9/2008 | Borck et al. |
| 2008/0241218 A1 | 10/2008 | McMorrow et al. |
| 2008/0243113 A1 | 10/2008 | Shastri et al. |
| 2008/0243230 A1 | 10/2008 | Lootz et al. |
| 2008/0243231 A1 | 10/2008 | Flanagan et al. |
| 2008/0243234 A1 | 10/2008 | Wilcox |
| 2008/0243240 A1 | 10/2008 | Doty et al. |
| 2008/0243242 A1 | 10/2008 | Kappelt et al. |
| 2008/0249600 A1 | 10/2008 | Atanasoska et al. |
| 2008/0249615 A1 | 10/2008 | Weber |
| 2008/0255508 A1 | 10/2008 | Wang |
| 2008/0255509 A1 | 10/2008 | Wang |
| 2008/0262589 A1 | 10/2008 | Nagura |
| 2008/0268308 A1 | 10/2008 | Schilling et al. |
| 2008/0269872 A1 | 10/2008 | Lootz et al. |
| 2008/0288048 A1 | 11/2008 | Rolando et al. |
| 2008/0290467 A1 | 11/2008 | Shue et al. |
| 2008/0294236 A1 | 11/2008 | Anand et al. |
| 2008/0294246 A1 | 11/2008 | Scheuermann |
| 2008/0306584 A1 | 12/2008 | Kramer-Brown |
| 2009/0005862 A1 | 1/2009 | Nakatani et al. |
| 2009/0012599 A1 | 1/2009 | Broome et al. |
| 2009/0018639 A1 | 1/2009 | Kuehling |
| 2009/0018647 A1 | 1/2009 | Benco et al. |
| 2009/0018648 A1 | 1/2009 | Wittchow |
| 2009/0022771 A1 | 1/2009 | Lynn et al. |
| 2009/0024199 A1 | 1/2009 | Birdsall et al. |
| 2009/0024209 A1 | 1/2009 | Ozdil et al. |
| 2009/0024210 A1 | 1/2009 | Klocke et al. |
| 2009/0024211 A1 | 1/2009 | Wittchow |
| 2009/0028785 A1 | 1/2009 | Clarke |
| 2009/0030494 A1 | 1/2009 | Stefanadis et al. |
| 2009/0030500 A1 | 1/2009 | Weber et al. |
| 2009/0030504 A1 | 1/2009 | Weber et al. |
| 2009/0030506 A1 | 1/2009 | Klocke et al. |
| 2009/0030507 A1 | 1/2009 | Klocke et al. |
| 2009/0035351 A1 | 2/2009 | Berglund et al. |
| 2009/0043330 A1 | 2/2009 | To |
| 2009/0043374 A1 | 2/2009 | Nakano |
| 2009/0043380 A1 | 2/2009 | Blaha et al. |
| 2009/0048660 A1 | 2/2009 | Adden |
| 2009/0062905 A1 | 3/2009 | Moore, Jr. et al. |

(56) References Cited

U.S. PATENT DOCUMENTS

| | | |
|---|---|---|
| 2009/0069884 A1 | 3/2009 | Mueller |
| 2009/0076588 A1 | 3/2009 | Weber |
| 2009/0076596 A1 | 3/2009 | Adden et al. |
| 2009/0081293 A1 | 3/2009 | Murase et al. |
| 2009/0081450 A1 | 3/2009 | Ascher et al. |
| 2009/0088831 A1 | 4/2009 | Goto |
| 2009/0088834 A1 | 4/2009 | Wang |
| 2009/0093871 A1 | 4/2009 | Rea et al. |
| 2009/0095715 A1 | 4/2009 | Sabaria |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118819 A1 | 5/2009 | Merz et al. |
| 2009/0118820 A1 | 5/2009 | Gregorich et al. |
| 2009/0118821 A1 | 5/2009 | Scheuermann et al. |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0124956 A1 | 5/2009 | Swetlin et al. |
| 2009/0131540 A1 | 5/2009 | Hiromoto et al. |
| 2009/0143855 A1 | 6/2009 | Weber et al. |
| 2009/0149942 A1 | 6/2009 | Edelman et al. |
| 2009/0157165 A1 | 6/2009 | Miller et al. |
| 2009/0157172 A1 | 6/2009 | Kokate et al. |
| 2009/0164002 A1 | 6/2009 | Becher et al. |
| 2009/0171452 A1 | 7/2009 | Yamamoto et al. |
| 2009/0177273 A1 | 7/2009 | Piveteau et al. |
| 2009/0182290 A1 | 7/2009 | Harder et al. |
| 2009/0182337 A1 | 7/2009 | Stopek et al. |
| 2009/0182425 A1 | 7/2009 | Duda et al. |
| 2009/0192571 A1 | 7/2009 | Stett et al. |
| 2009/0192594 A1 | 7/2009 | Borck |
| 2009/0192595 A1 | 7/2009 | Nagura et al. |
| 2009/0192596 A1 | 7/2009 | Adden |
| 2009/0196899 A1 | 8/2009 | Birdsall et al. |
| 2009/0198320 A1 | 8/2009 | Mueller et al. |
| 2009/0202610 A1 | 8/2009 | Wilson |
| 2009/0204203 A1 | 8/2009 | Allen et al. |
| 2009/0208428 A1 | 8/2009 | Hill et al. |
| 2009/0208555 A1 | 8/2009 | Kuttler et al. |
| 2009/0214373 A1 | 8/2009 | Stinson et al. |
| 2009/0220612 A1 | 9/2009 | Perera |
| 2009/0228037 A1 | 9/2009 | Rego |
| 2009/0240323 A1 | 9/2009 | Wilcox |
| 2009/0254171 A1 | 10/2009 | Heikkila |
| 2009/0259300 A1 | 10/2009 | Dorogy, Jr. et al. |
| 2009/0264979 A1 | 10/2009 | Kao et al. |
| 2009/0270979 A1 | 10/2009 | Adden |
| 2009/0274737 A1 | 11/2009 | Borck |
| 2009/0281613 A1 | 11/2009 | Atanasoska et al. |
| 2009/0287301 A1 | 11/2009 | Weber |
| 2009/0287302 A1 | 11/2009 | Thomas et al. |
| 2009/0306584 A1 | 12/2009 | Schmidtlein et al. |
| 2009/0306756 A1 | 12/2009 | Cho et al. |
| 2009/0306765 A1 | 12/2009 | Weber |
| 2009/0306766 A1 | 12/2009 | McDermott et al. |
| 2009/0311300 A1 | 12/2009 | Wittchow |
| 2009/0312807 A1 | 12/2009 | Boudreault et al. |
| 2009/0319035 A1 | 12/2009 | Terry |
| 2009/0324684 A1 | 12/2009 | Atanasoska et al. |
| 2009/0326638 A1 | 12/2009 | Atanasoska et al. |
| 2010/0008970 A1 | 1/2010 | O'Brien et al. |
| 2010/0010621 A1 | 1/2010 | Klocke |
| 2010/0010640 A1 | 1/2010 | Gerold et al. |
| 2010/0015206 A1 | 1/2010 | Flanagan et al. |
| 2010/0016940 A1 | 1/2010 | Shokoohi et al. |
| 2010/0021523 A1 | 1/2010 | Scheuermann et al. |
| 2010/0023112 A1 | 1/2010 | Borck et al. |
| 2010/0023116 A1 | 1/2010 | Borck et al. |
| 2010/0028436 A1 | 2/2010 | Ohrlander et al. |
| 2010/0030326 A1 | 2/2010 | Radhakrishnan et al. |
| 2010/0034899 A1 | 2/2010 | Harder et al. |
| 2010/0042205 A1 | 2/2010 | Atanasoska et al. |
| 2010/0042206 A1 | 2/2010 | Yadav et al. |
| 2010/0047312 A1 | 2/2010 | Wittchow |
| 2010/0047324 A1 | 2/2010 | Fritz et al. |
| 2010/0049146 A1 | 2/2010 | Nielsen et al. |
| 2010/0049296 A1 | 2/2010 | Sarasam et al. |
| 2010/0049299 A1 | 2/2010 | Popowski et al. |
| 2010/0049300 A1 | 2/2010 | Harder |
| 2010/0055151 A1 | 3/2010 | Flanagan |
| 2010/0057188 A1 | 3/2010 | Weber |
| 2010/0057197 A1 | 3/2010 | Weber et al. |
| 2010/0070024 A1 | 3/2010 | Venturelli et al. |
| 2010/0075162 A1 | 3/2010 | Yang et al. |
| 2010/0076544 A1 | 3/2010 | Hoffmann et al. |
| 2010/0076556 A1 | 3/2010 | Tomantschger et al. |
| 2010/0081735 A1 | 4/2010 | Mao et al. |
| 2010/0082092 A1 | 4/2010 | Gerold |
| 2010/0087910 A1 | 4/2010 | Weber |
| 2010/0087911 A1 | 4/2010 | Mueller |
| 2010/0087914 A1 | 4/2010 | Bayer et al. |
| 2010/0087915 A1 | 4/2010 | Bayer et al. |
| 2010/0087916 A1 | 4/2010 | Bayer et al. |
| 2010/0092535 A1 | 4/2010 | Cook et al. |
| 2010/0106243 A1 | 4/2010 | Wittchow |
| 2010/0119576 A1 | 5/2010 | Harder et al. |
| 2010/0119581 A1 | 5/2010 | Gratz et al. |
| 2010/0121432 A1 | 5/2010 | Klocke et al. |
| 2010/0125325 A1 | 5/2010 | Allen et al. |
| 2010/0125328 A1 | 5/2010 | Flanagan |
| 2010/0131050 A1 | 5/2010 | Zhao |
| 2010/0131052 A1 | 5/2010 | Kappelt et al. |
| 2010/0161031 A1 | 6/2010 | Papirov et al. |
| 2010/0217370 A1 | 8/2010 | Scheuermann et al. |
| 2011/0313510 A1 | 12/2011 | Gale et al. |
| 2012/0080189 A1 | 4/2012 | Marya et al. |

FOREIGN PATENT DOCUMENTS

| | | |
|---|---|---|
| CA | 2 235 031 | 10/1998 |
| CA | 2 346 857 | 5/2000 |
| CA | 2 371 800 | 8/2000 |
| DE | 198 11 033 | 8/1999 |
| DE | 198 56 983 | 12/1999 |
| DE | 103 57 281 | 7/2005 |
| DE | 103 61 941 | 7/2005 |
| DE | 10 2006 38236 | 2/2008 |
| EP | 0 006 544 | 6/1979 |
| EP | 0 337 035 | 10/1989 |
| EP | 0 615 769 | 9/1994 |
| EP | 0 923 389 | 7/1998 |
| EP | 0 923 912 | 6/1999 |
| EP | 0 966 979 | 12/1999 |
| EP | 0 972 563 | 1/2000 |
| EP | 1 054 644 | 11/2000 |
| EP | 1 071 490 | 1/2001 |
| EP | 1 222 901 | 7/2002 |
| EP | 1 260 214 | 11/2002 |
| EP | 1 270 023 | 1/2003 |
| EP | 1 273 314 | 1/2003 |
| EP | 1 370 306 | 12/2003 |
| EP | 1 389 471 | 2/2004 |
| EP | 1 393 766 | 3/2004 |
| EP | 1 419 793 | 5/2004 |
| EP | 0 951 877 | 6/2004 |
| EP | 0 875 218 | 2/2005 |
| EP | 1 733 746 | 12/2006 |
| EP | 1 752 167 | 2/2007 |
| EP | 1 465 552 | 5/2007 |
| EP | 1 835 042 | 9/2007 |
| EP | 1 750 780 | 10/2007 |
| EP | 1 562 565 | 3/2008 |
| EP | 1 642 551 | 12/2008 |
| EP | 1 653 885 | 4/2009 |
| EP | 1 632 256 | 9/2009 |
| EP | 1 703 858 | 10/2009 |
| EP | 2 139 535 | 1/2010 |
| EP | 1 883 380 | 3/2010 |
| EP | 2 189 169 | 5/2010 |

(56) References Cited

FOREIGN PATENT DOCUMENTS

| | | |
|---|---|---|
| JP | 06-306298 | 11/1992 |
| JP | 06-292716 | 10/1994 |
| JP | 10295824 A | 11/1998 |
| JP | 2001511049 A | 8/2001 |
| JP | 2003503157 | 1/2003 |
| JP | 2003-052834 | 2/2003 |
| JP | 2003-169846 | 6/2003 |
| JP | 2003-250880 | 9/2003 |
| JP | 2003-526386 | 9/2003 |
| JP | 2003275228 A | 9/2003 |
| JP | 2004-121827 | 4/2004 |
| JP | 2005168937 | 6/2005 |
| JP | 2007307132 A | 11/2007 |
| RU | 2 218 242 | 12/2003 |
| WO | WO 93/04118 | 3/1993 |
| WO | WO 97/11724 | 4/1997 |
| WO | 98/29025 | 7/1998 |
| WO | WO 98/48851 | 11/1998 |
| WO | WO9902195 A2 | 1/1999 |
| WO | 99/33410 | 7/1999 |
| WO | WO 99/47077 | 9/1999 |
| WO | WO 99/64580 | 12/1999 |
| WO | WO 00/25841 | 5/2000 |
| WO | WO 00/48660 | 8/2000 |
| WO | WO 00/51136 | 8/2000 |
| WO | 00/54704 | 9/2000 |
| WO | WO 00/66190 | 11/2000 |
| WO | WO0101957 A1 | 1/2001 |
| WO | 01/32072 | 5/2001 |
| WO | WO 01/49338 | 7/2001 |
| WO | WO 01/78906 | 10/2001 |
| WO | 01/80920 | 11/2001 |
| WO | 01/87371 | 11/2001 |
| WO | 02/39875 | 5/2002 |
| WO | WO 02/45764 | 6/2002 |
| WO | WO 02/47739 | 6/2002 |
| WO | WO 02/053202 A1 | 7/2002 |
| WO | 02/076523 | 10/2002 |
| WO | WO 03/002243 A2 | 1/2003 |
| WO | WO 03/013396 | 2/2003 |
| WO | 03/035123 | 5/2003 |
| WO | 03/035134 | 5/2003 |
| WO | WO 03/035131 | 5/2003 |
| WO | WO 03/035278 | 5/2003 |
| WO | 03/046062 | 6/2003 |
| WO | 03/068285 | 8/2003 |
| WO | WO 03/063733 A1 | 8/2003 |
| WO | WO 03/094990 | 11/2003 |
| WO | 2004/025332 | 3/2004 |
| WO | 2004/026361 | 4/2004 |
| WO | 2004/029313 | 4/2004 |
| WO | 2004/043292 | 5/2004 |
| WO | WO 2004/093643 | 11/2004 |
| WO | WO2004110515 A1 | 12/2004 |
| WO | 2005/025449 | 3/2005 |
| WO | WO2005042045 A1 | 5/2005 |
| WO | WO 2005/065576 | 7/2005 |
| WO | WO2005065576 A1 | 7/2005 |
| WO | 2005/079335 | 9/2005 |
| WO | WO2005084582 A1 | 9/2005 |
| WO | WO 2005/110395 | 11/2005 |
| WO | WO 2005/118019 | 12/2005 |
| WO | WO2005117752 A1 | 12/2005 |
| WO | WO 2006/008739 | 1/2006 |
| WO | WO 2006/060033 | 6/2006 |
| WO | WO 2006/060534 | 6/2006 |
| WO | WO 2006/065356 | 6/2006 |
| WO | WO 2006/077154 | 7/2006 |
| WO | 2006/080381 | 8/2006 |
| WO | 2006/097503 | 9/2006 |
| WO | 2006/104644 | 10/2006 |
| WO | WO 2006/108065 | 10/2006 |
| WO | WO 2007/005806 | 1/2007 |
| WO | WO 2007/013102 | 2/2007 |
| WO | WO 2007/018931 | 2/2007 |
| WO | WO 2007/024552 | 3/2007 |
| WO | WO 2007/035791 | 3/2007 |
| WO | 2007/079363 | 7/2007 |
| WO | WO 2007/079636 | 7/2007 |
| WO | WO 2007/082147 | 9/2007 |
| WO | 2007/139668 | 12/2007 |
| WO | 2008/003450 | 3/2008 |
| WO | 2008/034048 | 3/2008 |
| WO | 2008/034066 | 3/2008 |
| WO | 2008/036549 | 3/2008 |
| WO | 2008/036554 | 3/2008 |
| WO | WO 2008/062414 | 5/2008 |
| WO | 2008/092436 | 8/2008 |
| WO | 2008/106271 | 9/2008 |
| WO | 2008/118606 | 10/2008 |
| WO | WO 2008/117315 | 10/2008 |
| WO | 2009/045773 | 4/2009 |

OTHER PUBLICATIONS

Bach et al., "Corrosion Protection and Repassivation After the Deformation of Magnesium Alloys Coated With a Protective Magnesium Fluoride Layer", JOM, p. 343, Nov. 2004.

Yamaguchi et al., "Mg2Si Coating Technology on Magnesium Alloys to Improve Corrosion and Wear Resistance", JOM, p. 343, Nov. 2004.

Kutsenko et al., "Structural changes in Mg alloy induced by plasma immersion ion implantation of Ag", Acta Materialia, 52, pp. 4329-4335, 2004.

Heublein et al., "Biocorrosion of magnesium alloys: a new principle in cardiovascular implant technology?", Heart, 89, pp. 651-656, 2003.

Niemeyer et al., "Magnesium alloys as biodegradable metallic implant materials for cardiovascularic and orthopaedic surgery" Euromat 2001, $7^{th}$ European Conference on Advanced Materials and Processes, Jun. 10-14, 2001.

Park et al., Microstructural change and precipitation hardening in melt-spun Mg-X-Ca alloys, Science and Technology of Advanced Materials, 2, pp. 73-78, 2001.

Peuster et al., "A novel approach to temporary stenting: degradable cardiovascular stents produced from corrodible metal-results 6-18 months after implantation into New Zealand white rabbits", Heart, vol. 86, No. 5, Nov. 2001.

Heublein et al., "Local Tissue Engineering by Biocorrosion Vision or Reality?", The American Journal of Cardiology, TCT Abstracts/Poster, Oct. 16, 2000.

Heublein et al., "Bio-corrosion—a new principle for temporary cardiovascular implants?", European Heart Journal, Journal of the European Society of Cardiology, vol. 21, Aug./Sep. 2000.

Haferkamp et al., "Magnesium-Base-Alloys as Implant-Material Steps to the Production of Thin Components", Magnesium 2000, pp. 159-164, Feb. 22-24, 2000.

Heublein et al., "Degradation of Metallic Alloys—A New Principle in Stent Technology?", JACC, Feb. 2000.

Heublein et al., "Degradation of Metallic Alloys—A New Principle in Stent Technology?", The American Journal of Cardiology, Eleventh Annual Symposium Transcatheter Cardiovascular Therapeutics Abstracts, Sep. 22, 1999.

Brückner et al., "Metal plasma immersion ion implantation and deposition (MPIIID): chromium on magnesium", Surface and Coatings Technology, 103-104, pp. 227-230, 1998.

Yue et al., "Improvement in the Corrosion Resistance of Magnesium ZK60/SiC Composite by Excimer Laser Surface Treatment", Scripta Materialia, vol. 38, No. 2, pp. 191-198, 1998.

Weber et al., "Hardness and corrosion resistance of single-phase nitride and carbide on ion", Materials Science and Engineering, A199, pp. 205-210, 1995.

Ferrando, "Review of Corrosion and Corrosion Control of Magnesium Alloys and Composites", J. Mater. Eng., 11, pp. 299-313, 1989.

Baurschmidt et al., "The Electrochemical Aspects of the Thrombogenicity of a Material", Journal of Bioengineering, vol. 1, pp. 261-278, 1977.

Sawyer et al., "Electrochemical Criteria in the Choice of Materials used in Vascular Prostheses", Biophysical Mechanisms in Vascular Homeostasis and Intravascular Thrombosis, pp. 337-348, 1965.

(56) References Cited

OTHER PUBLICATIONS

International Preliminary Report on Patentability received in PCT/US2007/060137, mailed Jul. 17, 2008, 7 pages.
U.S. Appl. No. 10/849,742, Chen et al.
U.S. Appl. No. 60/826,002, filed Sep. 18, 2006, Girton et al.
U.S. Appl. No. 60/862,318, filed Oct. 20, 2006, Atanasoska et al.
U.S. Appl. No. 60/845,136, filed Sep. 15, 2006, Weber et al.
"Galvanic cell" printout from wikipedia, 2 pgs, printed Oct. 28, 2005.
"Galvanic corrosion", http://www.corrosion-doctors.org/Aircraft/galvdefi.htm, 3 pgs., printed Oct. 28, 2005.
"Galvanic series" printout from Wikipedia, p. 1 of 2, printed Oct. 28, 2005.
"Best of the ACC Scientific Session 2002," *Rev. Cardiovasc. Med.*, 2002, 3(2):85-104.
"Corrosion Theory and Corrosion Protection," EM 1110-2-3400, 1995, 8 pages.
Aghion et al., "Newly Developed Magnesium Alloys for Powertrain Applications," *JOM*, 2003, p. 30.
Andión et al., "Corrosion behaviour at the interface of steel bars embedded in cement slurries. Effect of phenol polymer coatings," *Corrosion Science*, 2002, 44:2805-2816.
Antipov et al., "Polyelectrolyte Multilayer Capsule Permeability Control," *Colloids and Surfaces A: Physiochem. Eng. Aspects*, 2002, 198-200, 535-541.
Antipov et al., "Polyelectrolyte Multilayer Capsules as Vehicles with Tunable Permeability," *Advances in Colloid and Interface Science*, 2004, 111:49-61.
Arts et al., "Polyphenols and disease risk in epidemiologic studies," *Am. J. Clin. Nutr.*, 2005, 81:317S-325S.
Artyukhin et al., "Layer-by-Layer Electrostatic Self-Assembly of Polyelectrolyte Nanoshells on Individual Carbon Nanotube Templates," *Langmuir*, 2004, 20:1442-1448.
Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.
Berkland et al., "Controlling Surface Nano-structure Using Flow-Limited Field-Injection Electrostatic Spraying (FFESS) of poly(D,L-lactide-*co*-glycolide)," *Biomaterials*, 2004, 25:5649-5658.
Berry et al., "Functionalisation of magnetic nanoparticles for applications in biomedicine," *J. Phys. D: Appl. Phys.*, 2003, 36:R198-R206.
Bolz et al., "Effect of smooth, porous and fractal surface structure on the properties of an interface," *J. Materials Science: Materials in Medicine*, 1995, 6:844-848.
Brandau et al., "Nanoporous Ceramic Coatings for Synthesis of Radioactive Implants," *Journal of Nuclear Medicine Abstract Book*, Jun. 7, 2000, p. 244P, Abstract No. 1076.
Buescher et al., "Characterization of Wet-Chemically Nanostructured Stainless Steel Surfaces," *Mat. Res. Soc. Symp. Proc.*, 2001, 676:1-6.
Caruso et al., "Ultrathin Molybdenum Polyoxometalate-Polyelectrolyte Multilayer Films," *Langmuir*, 1998, 14:3462-3465.
Casan-Pastor et al., "Polyoxometalates: From Inorganic Chemistry to Materials Bioscience," *Frontiers in Bioscience*, 2004, 9:1759-1770.
Chaieb et al , "Inhibition of the corrosion of steel in 1 M HC1 by eugenol derivatives," *Applied Surface Science*, 2005, 246:199-206.
Changwen et al., "Polyoxometalate-based organic-inorganic hybrid materials"; http://www.solgel.com/articles/oct01/changwen.asp, Retrieved from the Internet on Nov. 1, 2004 (17 pages).
Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.
International Search Report/Written Opinion in PCT/US05/16600 mailed May 4, 2006, 15 pages.
International Preliminary Report on Patentability in PCT/US05/16600 mailed Nov. 30, 2006, 7 pages.
International Preliminary Report on Patentability in PCT/US07/78476 mailed Mar. 26, 2009, 7 pages.
Authorized Officer Simin Baharlou, International Search Report/Written Opinion in PCT/US07/66568 mailed Oct. 8, 2007, 11 pages.
Authorized Officer Simin Baharlou, International Preliminary Report on Patentability in PCT/US07/66568 mailed Oct. 23, 2008, 10 pages.
International Search Report/Written Opinion in PCT/US07/78505 mailed Mar. 4, 2008, 10 pages.
International Preliminary Report on Patentability in PCT/US07/78505 mailed Mar. 26, 2009, 7 pages.
Authorized Officer Athina Nickitas-Etienne, International Search Report/Written Opinion in PCT/US07/78449, mailed Jan. 13, 2009, 24 pages.
Authorized Officer Athina Nickitas-Etienne, International Preliminary Report on Patentability in PCT/US07/78449 mailed Mar. 26, 2009, 9 pages.
Authorized Officer Simin Baharlou, International Search Report/Written Opinion in PCT/US07/75072 mailed Jan. 25, 2008, 11 pages.
Authorized Officer Simin Baharlou, International Preliminary Report on Patentability in PCT/US07/75072 mailed Feb. 12, 2009, 9 pages.
International Search Report/Written Opinion in PCT/US07/78429 mailed Mar. 28, 2008, 13 pages.
International Preliminary Report on Patentability in PCT/US07/78429 mailed Apr. 2, 2009, 8 pages.
International Search Report/Written Opinion in PCT/US07/78411 mailed Mar. 6, 2008, 12 pages.
International Preliminary Report on Patentability in PCT/US07/78411 mailed Feb. 4, 2009, 8 pages.
Authorized Officer Elisabeth Reinecke, International Search Report/Written Opinion in PCT/US07/60137 mailed Jul. 27, 2007, 20 pages.
International Preliminary Report on Patentability in PCT/US07/78412 mailed Apr. 2, 2009, 7 pages.
Authorized Officer Trudy Hinterwimmer, International Search Report/Written Opinion in PCT/US07/78412 mailed Mar. 3, 2008, 10 pages.
Authorized Officer Joëlle Gerber, International Search Report/Written Opinion in PCT/US07/78450 mailed Nov. 19, 2008, 17 pages.
International Preliminary Report on Patentability in PCT/US07/78450 mailed Mar. 26, 2009, 7 pages.
International Search Report/Written Opinion in PCT/US07/73839 mailed Apr. 16, 2008, 17 pages.
International Preliminary Report on Patentability in PCT/US07/73839 mailed Apr. 2, 2009, 10 pages.
Authorized Officer Cecilia Giel-Barragán Ramos, International Search Report/Written Opinion in PCT/US07/79841 mailed Feb. 4, 2009, 21 pages.
Authorized Officer Athina Nickitas-Etienne, International Preliminary Report on Patentability in PCT/US07/79841 mailed Apr. 30, 2009, 7 pages.
Authorized Officer Joëlle Gerber, International Search Report/Written Opinion in PCT/US07/88888 mailed Jul. 13, 2009, 24 pages.
Authorized Officer Nora Lindner, International Preliminary Report on Patentability in PCT/US07/88888 mailed Jul. 30, 2009, 11 pages.
Authorized Officer Véronique van Loon-Mégard, International Search Report/Written Opinion in PCT/US08/75976 mailed Nov. 25, 2008, 20 pages.
Authorized Officer Trudy Hinterwimmer, International Search Report/Written Opinion in PCT/US09/49422 mailed Aug. 24, 2009, 10 pages.
Damiani et al., "Vasorelaxant effects on eugenol on rat thoracic aorta," *Vascular Pharmacol.*, 2003, 40:59-66.
Dexter, "Galvanic Corrosion," MAS Note, University of Delaware Sea Grant Marine Advisory Service, 2003.
Di Mario et al., "MOONLIGHT: a controlled registry of an iridium-oxide coated stent with angiographic follow up," *Int. J. Cardiol.*, 2004, 95:329-331.
Dowling et al., "Anti-bacterial silver coatings exhibiting enhanced activity through the addition of Platinum," *Surf. & Coatings Tech.*, 2003, 163-164:637-640.

(56) References Cited

OTHER PUBLICATIONS

Duygu, "Controlled Release Systems," http://www.biomed.metu.edu.tr/courses/term_papers/contr-rel-sys_duygu.htm (Dec. 30, 2005).
Eniola and Hammer, "Characterization of biodegradable drug delivery vehicles with the adhesive properties of leukocytes II: effect of degradation on targeting activity," *Biomaterials*, 2005, 26:661-670.
Farhat et al., "Corrosion Control Using Polyelectrolyte Multilayers," *Electrochemical and Solid State Letters*, 2002, 5(4):B13-B15.
Fischer et al., "Hydrogen in magnesium alloys and magnesium interfaces: preparation, electronic properties and interdiffusion," *J. Less Common Metals*, 1991, 172:808-815.
Fontenier et al., "Study of a 'Platinum-Magnesium' Cell to Supply Current to a Pacemaker," *Bioelectrochemistry and Bioenergetics*, 1975, 2(2):106-123.
Frei, "On the Role of Vitamin C and Other Antioxidants in Atherogenesis and Vascular Dysfunction," *Proceedings—Society for Experimental Biology and Medicine*, 1999, 222:196-204.
Gomes et al., "Alternative tissue engineering scaffolds based on starch: processing methodologies, morphology, degradation and mechanical properties," *Materials Science and Engineering C*, 2002, 20:19-26.
Grassi et al., "Short-term administration of dark chocolate is followed by a significant increase in insulin sensitivity and a decrease in blood pressure in healthy persons," *Am. J. Clin. Nutr.*, 2005, 81(3):611-614.
Gray and Luan, "Protective coatings on magnesium and its alloys—a critical review," *J. Alloys Compounds*, 2002, 336:88-113.
Guo et al., "Multi-layer LB films of single-wall carbon nanotubes," *Physica B*, 2002, 323:235-236.
Guo et al., "Manipulation of single-wall carbon nanotubes into aligned molecular layers," *Chem. Phys. Lett.*, 2002, 362:314-318.
Gurib-Fakim, "Medicinal plants: Traditions of yesterday and drugs of tomorrow," *Molecular Aspects of Medicine*, 2006, 27:1-93.
Haferkamp et al., "Magnesium-Base-Alloys as Implant-Material Steps to the Production of Thin Components," *Magnesium*, 2000, 159-164.
Hau et al., "Surface-Chemistry Technology for Microfluidics," *J. Micromech. Microeng.*, 2003, 13:272-278.
Huang et al., "A Review on Polymer Nanofibers by Electro-spinning and their Applications in Nanocomposites," *Composites Science & Technology*, 2003, 63:2223-2253.
Ito et al., "Antioxidant action of eugenol compounds; role of metal ion in the inhibition of lipid peroxidation," *Food Chem. Toxicol.*, 2005, 43:461-466.
Ivanova and Ivanov, "Mechanisms of the extracellular antioxidant defend," *Experimental Pathology and Parasitology*, 2000, 4:49-59.
Jiang, "A review of wet impregnation—An alternative method for the fabrication of high performance and nano-structured electrodes of solid oxide fuel cells," *Materials Science and Engineering A*, 2006, 418:199-210.
Kean and Davies, "Cathodic Protection," 7 pages, 1981; http://www.npl.co.uk/upload/pdf/cathodic_protection.pdf.
Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.
Kim et al., "Effect of Anti-Oxidant (Carvedilol and Probucol) Loaded Stents in a Porcine Coronary Restenosis Model," *Circ. J.*, 2005, 69:101-106.
Kong et al., "Polyelectrolyte-functionalized multiwalled carbon nanotubes: preparation, characterization and layer-by-layer self assembly," *Polymer*, 2005, 46:2472-2485.
Kumar et al., "Polyanhydrides: an overview," *Advanced Drug Delivery Reviews*, 2002, 54:889-910.
Kurth et al., "Multilayer on Solid Planar Substrates: From Structure to Function", *Multi-layer Thin Films Sequential Assembly of Nanocomposite Materials*, 2003, Chapter 14, pp. 393-426.
Kurth et al., "Ultrathin Composite Films Incorporating the Nanoporous Isopolyoxomolybdate 'Keplerate' $(NH_4)_42[Mo_{132}O_{372}(CH_3COO)_{30}(H_2O)_{72}]$," *Chem. Mater.*, 2000, 12:2829-2831.
Lambert et al., "Inhibition of carcinogenesis by polyphenols: evidence from laboratory investifations," *Am. J. Clin. Nutr.*, 2005, 81:284S-291S.
Lee et al., "Retentive and compressive strengths of modified zinc oxide-eugenol cements," *J. Dentistry*, 2000, 28:69-75.
Liao et al., "Fabrication of porous biodegradable polymer scaffolds using a solvent merging/particulate leaching method," *J. Biomed. Mater. Res.*, 2002, 59(4):676-681.
Lin et al., "Micropatterning proteins and cells on polylactic acid and poly(lactide-*co*-glycolide)," *Biomaterials*, 2005, 26:3655-3662.
Liu et al., "Sol-gel deposited TiO2 film on NiTi surgical alloy for biocompatibility improvement," *Thin Solid Films*, 2003, 429:225-230.
Liu, *Introduction to Corrosion and Protection*, Corrosion and Protection Centre, School of Materials, The University of Manchester, 2006, 36 pages.
Liu et al., "Layer-By-Layer Ionic Self-Assembly of Au Colloids Into Multilayer Thin-Films with Bulk Metal Conductivity," *Chemical Physics Letters*, 1998, 298:315-319.
Liu et al., "Functional Polyoxometalate Thin Films via Electrostatic Layer-by-Layer Self-Assembly," *Journal of Cluster Science*, 2003, 14:405-419.
Maier et al., "High concentrations of magnesium modulate vascular endothelial cell behaviour in vitro," *Biochim. Biophys. Acta*, 2004, 1689:6-12.
Mamedov et al., "Molecular Design of Strong Single-Wall Carbon Nanotube/Polyelectrolyte Multilayer Composites," *Nature Materials*, 2002, 1:190-194.
Matsuoka et al., "Hyperthermia Using Magnetite Cationic Liposomes for Hamster Osteosarcoma," *BioMagnetic Research and Technology*, 2004, 2:3-8.
Medical Device Daily, "Conor Cites Positive 12-month Results for Its CoStar Stent", May 2005 (1 page).
Middleton and Tipton, "Synthetic Biodegradable Polymers as Medical Devices," http://www.devicelink.com.mpb/archive/98/03/002.html, Mar. 1998, 9 pages.
Mihailovic et al., "Unusual Magnetic State in Lithium-Doped $MoS_2$ Nanotubes," *Phys. Rev. Lett.*, 2003, 90 146401-1-4.
Mikos and Temenoff, "Formation of highly porous biodegradable scaffolds for tissue engineering," *Electronic Journal of Biotechnology*, 2000, 3(2):1-6.
Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.
Mohanty et al. "Evaluation of soft tissue response to a poly[urethane urea]," *Biomaterials*, 1992, 13(10):651-656.
Molnar and Garai, "Plant-derived anti-inflammatory compounds affect MIF tautomerase activity," *International Immunopharmacology*, 2005, 5:849-856.
Moskaug et al., "Polyphenols and glutathione synthesis regulation," *Am. J. Clin. Nutr.*, 2005, 81:277S-283S.
Naderi et al., "Effect of some volatile oils on the affinity of intact and oxidized low-density lipoproteins for adrenal cell surface receptors," *Mol. Cell. Biochem.*, 2004, 267:59-66.
Nilsson et al., "Development of a dosage method for electrochemical treatment of tumours: a simplified mathematical model," *Bioelectrochemistry and Bioenergetics*, 1998, 47:11-18.
Ou et al., "Protective effects of eugenol against oxidized LDL-induced cytotoxicity and adhesion molecule expression in endothelial cells," *Food Chem. Toxicol.*, 2006, 44:1485-1495.
Peuster et al., "Long-term biocompatibility of a corrodible peripheral iron stent in the porcine of descending aorta," *Biomaterials*, 2006, 27:4955-4962.
Prasse et al., "Electric Anisotropy of Carbon Nanofibre/Epoxy Resin Composites Due to Electric Field Induced Alignment," *Composites Science and Technology*, 2003, 63:1835-1841.

(56) References Cited

OTHER PUBLICATIONS

Ratnam et al., "Role of antioxidants in prophylaxis and therapy: A pharmaceutical perspective," *J. Controlled Release*, 2006, 113:189-207.
Remskar et al., "Self-Assembly of Subnanometer-Diameter Single-Wall MoS$_2$ Nanotubes," *Science*, 2001, 292:479-481.
Rezwan et al., "Biodegradable and bio active porous polymer/inorganic composite scaffolds for bone tissue engineering," *Biomaterials*, 2006, 27:3413-3431.
Rhule et al., "Polyoxometalates in Medicine," *Chem. Rev.*, 1998, 98:327-357.
Rutledge et al., "Electrostatic Spinning and Properties of Ultrafine Fibers," *National Textile Center Annual Report*, Nov. 2001, M01-D22, pp. 1-10.
Ryan et al., "Fabrication methods of porous metals for use in orthopaedic applications," *Biomaterials*, 2006, 27:2651-2670.
Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.
Satoh et al., "Effect of Antioxidants on Radical Intensity and Cytotoxic Activity of Eugenol," *Anticancer Res.*, 1998, 18:1549-1552.
Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.
Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.
Schetky, "Shape Memory Alloys," *Encyclopedia of Chemical Technology* (3rd ed.), 1962, John Wiley & Sons, 20:726.
Shaw, "Corrosion Resistance of Magnesium Alloys," *ASM Handbook vol. 13A: Corrosion: Fundamentals, Testing, and Protection*, 2003, 5 pages.
Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.
Shi et al., "A novel electrically conductive and biodegradable composite made of polypyrrole nanoparticles and polylactide," *Biomaterials*, 2004, 25:2477-2488.
Shin, "Experimental Characterization of Electrospinning: the Electrically Forced Jet and Instabilities," *Polymer*, 2001, 42:9955-9967.
Singh et al., "Electrocatalytic Activity of Electrodeposited Composite Films of Polypyrrole and CoFe$_2$O$_4$ Nanoparticles Towards Oxygen Reduction Reaction," *Electrochimica Acta*, 2004, 49:4605-4612.
Song et al., "Galvanic corrosion of magnesium alloy AZ91D in contact with an aluminium alloy, steel and zinc," *Corrosion Science*, 2004, 46:955-977.
Stoclet et al., "Vascular protection by dietary polyphenols," *Eur. J. Pharmacol.*, 2004, 500:299-313.
Straumal et al., "Vacuum arc deposition of protective layers on glass and polymer," *Thin Solid Films*, 2001, 383:224-226.
Suhaj, "Spice antioxidants isolation and their antiradical activity: a review," *J. Food Composition and Analysis*, 2006, 19:531-537.
Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.
Suslick et al., "The Photochemistry of Chromium, Manganese, and Iron Porphyrin Complexes," *J. Chem.*, 1992, 16:633-642.
Tada et al., "Distribution of pH during galvanic corrosion of a Zn/steel couple," *Electrochimica Acta*, 2004, 49:1019-1026.
Tan et al., "Systematic Parameter Study for Ultra-Fine Fiber Fabrication Via Electrospinning Process," *Polymer*, 2005, 46:6128-6134.
Vermette et al., "Immobilized Liposome Layers for Drug Delivery Applications," *J. Controlled Release*, 2002, 80:179-195.
von Euler et al., "Cell proliferation and apoptosis in rat mammary cancer after electrochemical treatment (EChT)," *Bioelectrochemistry*, 2004, 62:57-65.
Vrbanic et al., "Air-Stable Monodispersed Mo$_6$S$_3$I$_6$ Nanowires," *Nanotechnology*, 2004, 15:635-638.
Wallerath et al., "A blend of polyphenols explains the stimulatory effect of red wine on human endothelial No synthase," *Nitric Oxide*, 2005, 12(2):97-104.
Wan et al., "Influence of Plasma Immersion Ion Implantation on Corrosion Properties of Magnesium," South Jiaotong University, Chengdu, 2005.
Wang et al., "Nonlinear optical properties of thin iron films grown on MgO (100) by pulsed laser deposition," *Thin Solid Films*, 2005, 471:86-90.
Wang et al., "Characterisation of Severely Deformed Austenitic Stainless Steel Wire," *Materials Science and Technology*, 2005, 21:1323-1328.
Wang, "Recent development of non-platinum catalysts for oxygen reduction reaction," *J. Power Sources*, 2005, 152:1-15.
Weber et al., "Hardness and corrosion resistance of single-phase nitride and carbide on ion," *Materials Science and Engineering*, 1995, 99:205-210.
Weh et al., "Evolution of afractal-like surface structures in layers of polyacrylonitrile solutions by interfacial dynamic processes," *J. Colloid and Interface Science*, 2004, 271:407-415.
Widmer et al., "Manufacture of porous biodegradable polymer conduits by an extrusion process for guided tissue regeneration," *Biomaterials*, 1998, 19:1945-1955.
Wieneke et al., "Stent Coating: A New Approach in Interventional Cardiology," *Herz*, 2002, 27(6):518-526.
Williamson et al., "Bioavailability and bioefficacy of polyphenols in humans. II. Review of 93 intervention studies," *Am. J. Clin. Nutr.*, 2005, 81:243S-255S.
Witte et al., "In vitro and in vivo corrosion measurements of magnesium alloys," *Biomaterials*, 2006, 27:1013-1018.
Yi et al., "Characterization of a bioactive nanotextured surface created by controlled chemical oxidation of titanium," *Surface Science*, 2006, 600:4613-4621.
You et al., "The Effect of Calcium Additions on the Oxidation Behavior in Magnesium Alloys," *Scripta Mat.*, 2000, 42:1089-1094.
Yu and Uan, "Sacrificial Mg film anode for cathodic protection of die cast Mg-9-wt.%-1 wt.%Zn alloy in NaCl aqueous solution," *Scripta Mat.*, 2006, 54:1253-1257.
Zeta Potential—An Introduction in 30 Minutes, Technical Note; http://www.nbtc.cornell.edu/facilities/downloads/Zeta%20potential%20-%20An%20introduction%20in%2030%20minutes.pdf Retrieved from the Internet on May 9, 2005 (6 pages).
Zhang et al., "Natural Polyelectrolyte Films Based on Layer-by-Layer Deposition of Collagen and Hyaluronic Acid," *Biomaterials*, 2005, 26:3353-3361.
Zhang et al., "Improving multilayer films endurance by photoinduced interaction between Dawson-type polyoxometalate and diazo resin," *Materials Chemistry and Physics*, 2005, 90:57-52.
Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.
Zhou et al., "Drug-loaded, Magnetic, hollow silica nanocomposites for nanomedicine," *Nanomedicine: Nanotechnology, Biology and Medicine*, 2005, 1:233-237.
Zucchi et al., "Influence of a silane treatment on the corrosion resistance of a WE43 magnesium alloy," *Surface Coatings Technol.*, 2006, 200:4136-4143.
International Preliminary Report on Patentability from PCT/US08/75976 dated Mar. 25, 2010, 8 pages.
Deepwater, "Galvanic Series," http://corrosion-doctors.org/definitions/galvanic-series.htm> on Mar. 11, 2011, 5 pages.
Wikipedia, the Free Encyclopedia, "Galvanic Corrosion." <http://en.wikipedia.org/wiki/Galvanic_corrosion> on Mar. 11, 2011, 7 pages.
Authorized Officer Mary Celine, International Search Report from PCT/US2010/060412 mailed Feb. 21, 2011, 10 pages.

(56) References Cited

OTHER PUBLICATIONS

Dumas et al., "Characterization of magnesium fluoride thin films produced by argon ion beam-assisted deposition," *Thin Solid Films*, 2001, pp. 61-68.
Authorized Officer Razik Menidjel, International Preliminary Report on Patentability from PCT/US09/059424, mailed May 5, 2011, 8 pages.
Macias et al., "Electrospun mesoporous metal oxide fibers," *Microporous and Mesoporous Materials*, 2005, 86: 1-13.
Viswanathamurthi et al., "Preparation and morphology of niobuim oxide fibres by electrospinning," *Chemical Physics Letters*, 2003, 374: 79-84.
Authorized Officer Henrique Amaro, International Preliminary Report on Patentability from PCT/US09/043326 mailed Nov. 18, 2010, 7 pages.
Authorized Officer Jasmine Messemanne, International Search Report from PCT/US09/051965 mailed Aug. 20, 2010, 13 pages.
Authorized Officer Jasmine Messemanne, International Preliminary Report on Patentability from PCT/US09/051965 mailed Feb. 10, 2011, 8 pages.
Authorized Officer Antonio Espuch, International Preliminary Report on Patentability in PCT/US09/49422 mailed Jan. 13, 2011, 7 pages.
Authorized Officer Aurore Schneider, International Preliminary Report on Patentability from PCT/US2010/042772 mailed Feb. 4, 2011, 9 pages.
Authorized Officer Henrique Amaro, International Preliminary Report on Patentability in PCT/US2009/43326 mailed Nov. 18, 2010, 7 pages.
Authorized Officer Antoine Laurent, International Preliminary Report on Patentability in PCT/US09/046750 mailed Dec. 23, 2010, 8 pages.
Aaltonen, "Atomic Layer Deposition of Noble Metal Thin Films," University of Helsinki, Apr. 8, 2005, pp. 1-71.
Albion Research Notes, Newsletter, Oct. 1994, 3(4): 1-4.
Anand et al., "Ion-exchange resins: carrying drug delivery forward," *DDT*, 2001, 6: 905-914.
Anderson et al., "A new conductive polymer as a replacement for chrome conversion coatings," *2003 Aerospace Coatings Removel and Coatings Conference*, May 20-22, 2003, Colorado Springs, CO, 7 pages.
Ashtari et al. "An efficient method for recovery of target ssDNA based on amino-modified silica-coated magnetic nanoparticles" *Talanta* 67. (2005). 548-554.
Atta, "Electrochemical synthesis, characterization and some properties of a polymer derived from thioflavin S.," *European Polymer Journal*, 2005, 41: 3018-3025.
Australian Government, Department of Health and Aging, "Horizon Scanning Technology Prioritising Summary—Biodegradable stents for coronary artery disease," *Australia and New Zealand Horizon Scanning Network (ANZHSN)*, Aug. 2007, pp. 1-13.
Authorized officer Athina Nickitas-Etienne, International Preliminary Report on Patentability in PCT/US08/86639 mailed Jun. 24, 2010, 2 pages.
International Search Report/Written Opinion in PCT/US2008/86639 mailed Feb. 23, 2010, 8 pages.
International Search Report/Written Opinion in PCT/US2009/43326 mailed Aug. 6, 2009, 9 pages.
Balasubramanian et al. "Dispersion and Stability Studies of Resorcinarene-Encapsulated Gold Nanoparticles." *Langmuir*, 2002, 1676-3681.
Bao, Y. et al. "Preparation of functionalized and gold-coated cobalt nanocrystals for biomedical applications." *Journal of Magnetism and Magnetic Materials*, 2005, 293:15-19.
Bekesi et al., "Efficient Submircon Processing of Metals with Femto," *Appl. Phys. A.*, Published Oct. 25, 2002, pp. 355-357.
Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly(aniline-co-2-anisidine) films on stainless steel," *Progress in Organic Coatings*, 2005, 54: 63-72.
Bernkop-Schnurch, "Chitosan and its derivatives: potential excipients for peroral peptide delivery systems," *International J. of Pharmaceutics*, 2000, 194: 1-13.
Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.
Blanusa et al., "Chelators as Antidotes of Metal Toxicity Therapeutic and Experimental Aspects," *Current Medicinal Chemistry*, 2005, vol. 12, pp. 2771-2794.
Bosiers et al., "Absorbable Metal stent for CLI in Infrapopliteal lesions: 1 year results," *CX 2005 Global Endovascular Forum*, Apr. 2005, pp. 1-23.
Brunatto and Muzart, "Influence of the gas mixture flow on the processing parameters of hollow cathode discharge ion sintering," *J. Phys. D.: Appl. Phys.*, 2007, 40: 3937-3944.
Brunner et al., "Porosity Tailored Growth of Black Anodic Layers on Magnesium in an Organic Electrolyte," Journal of the Electrochemical Society, vol. 156 (2), Dec. 12, 2008, pp. C62-C66.
Chang et al., "Effect of Heat Treatment on Corrosion and Electrochemical behavior of Mg-3Nd-0.2Zn-0.4Zr (wt. %) alloy," *Science Direct, Electrochimica Acta 52*, 2007, 3160-3167.
Chang et al., "Templated sythesis of Gold-iron Alloy nanoparticles using pulsed laser deposition," *Nanotechnology*, vol. 17, 2006, pp. 5131-5135.
Chen et al., "Laser Cladding of Mg20A18o Powder on ZM5 Magnesium Alloy," *Corrosion Engineering, Science and Technology*, 2007, vol. 42, No. 2, pp. 130-136.
Cheng et al., "Electrogeneration and electrochemical properties of hybrid materials: polypyrrole doped with polyoxometalates $PW_{12-x}Mo_xO_{40}^{3-}$ (x=0,3,6,12)," *Synthetic Metals*, 2002, 129: 53-59.
Cho et al., "Gold-coated iron nanoparticles: a novel magnetic resonance agent for $T_1$ and $T_2$ weighted imaging," *Nanotechnology*, vol. 17, 2006, pp. 640-644.
Chou et al., "Electrochemical treatment of mouse and rat fibrosarcomas with direct current," *Bioelectromagnetics*, 1997, 18:14-24.
Cogger et al. "An Introduction to Electrochemical Impedance Measurement," *Solartron Analytical*, 1999, 2-14.
Conolly et al., "X-Ray microtomography studies of localized corrosion and transitions to stress corrosion cracking," *Materials Science and Technology*, 2006, vol. 22, No. 9, pp. 1076-1085.
Costa et al., "The effect of the magnetic field on the corrosion behavior of Nd—Fe—B permanent magnets." *Journal of Magnetism and Magnetic Materials*, 278, 2004, pp. 348-358.
Damen et al., "Paclitaxel esters of malic acid as prodrugs with improved water solubility," *Bioorganic & Medicinal Chemistry*, 2000, 8: 427-432.
Davies, "Changing the salt, changing the drug," *The Pharmaceutical Journal*, 2001, 266: 322-323.
De Geest et al., "Self-rupturing Microcapsules," *Adv. Mater.*, 2005, vol. 17, pp. 2357-2361.
de Witte, "Analysis of the principal component of external casing corrosion in deep wells," *J. Appl. Electrochem.*, 1985, 15: 325-334.
Di Mario et al., "Drug-eluting bioabsorbable magnesium stent," *J. Interventional Cardiol.*, 2004, 17(6): 391-395.
Duncan et al., "Polymer-drug conjugates, PDEPY and PELT: basic principles for design and transfer from the laboratory to clinic," *Journal of Controlled Release*, 2001, 74: 135-146.
Duncan, "The dawning era of polymer therapeutics," *Nature Reviews/Drug Discovery*, 2003, 2: 347-360.
Eggebrecht et al., "Novel Magnetic Resonance-Compatible Coronary Stent: The Absorbable Magnesium-Alloy Stent," *Circulation*, 2005, 112: 303-304.
Erbel et al., "Absorbierbare Stents-Eine Vielversprechende Neuerung?" *Urban & Vogel*, No. 4, 2007, pp. 308-319.
Erbel et al., "Temporary scaffolding of coronary arteries with bioabsorbable magnesium stents: a prospective, non-randomised multicentre trial," *Lancet*, 2007, vol. 369, pp. 1869-1875.

(56) References Cited

OTHER PUBLICATIONS

Erne et al., "The Road to Bioabsorbable Stents: Reaching Clinical Reality?" *Cardio Vascular and Interventional Radiology*, Sep. 26, 2005, pp. 11-16.
International Preliminary report on Patentability received in PCT/US2007/078417, mailed Mar. 26, 2009, 8 pages.
International Preliminary Report on Patentability, received in PCT/US2007/078407, mailed Mar. 26, 2009, 6 pages.
European Search Report from EP 10159664.1, mailed Jun. 4, 2010, 3 pages.
Falotico, "Cordis Fully Bioabsorbable Stent Program," *Euro PCR09*, May 22, 2009, pp. 1-21.
Fan et al., "Influence of Lanthanum on the microstructure, mechanical property and corrosion resistance of magnesium alloy," *J. Mater Sci*, 2006, vol. 41, pp. 5409-5416.
Fan et al., "Metallic Stents Coated with Bioabsorable Polymers," *Cardiac Interventions Today*, Jun./Jul. 2009, pp. 42-49.
Feng et al., "Sonochemical preparation of photochromic nanocomposite thin films based on polyoxometalates well dispersed in polyacrylamide," *Journal of Solid State Chemistry*, 2002, 169: 1-5.
Feng et al., "Superplasticity and texture of SiC whiskers in a magnesium-based composite," *Scripta Materialia*, 2005, 53: 361-365.
Ferguson et al., "Corrosion—Fatigue Performance of Magnesium Alloys," *International Journal of Modern Physics B*, vol. 17, Nos. 8 & 9, 2003, pp. 1601-1607.
Fischer et al., "Determination of in-vivo corrosion rates of degradable implants by SR-microtomography," date unknown, pp. 1-2.
Fraunhofer EZRT, "Quantitative material analysis by dual energy computed tomography for industrial NDT applications," 2009, 1 pg.
Fraunhofer IIS—Poster (German), "Prinzip der hochauflösenden Comptuertomographie," 2009, 1 page.
Gabrielli, Claude. "Use and Applications of Electrochemical Impedance Techniques," *Solartron Analytical*, 1997, 1-102.
Garner et al., "Polypyrrole-heparin composites as stimulus-responsive substrates for endothelial cell growth," *J. Biomed. Mater. Res.*, 1999, 44: 121-129.
Gettleman et al., "Measurement of in vivo corrosion rates in baboons, and correlation with in vitro tests," Journal of Dental Research, 1980, 59: 689-707.
Gettleman et al., "Materials Science: Measurement of in vivo Corrosion Rates in Baboons, and Correlation with in vitro Tests," *Journal of Dental Research*, 1980, vol. 59, pp. 689-707.
Griffiths et al., "Future devices: bioabsorbable stents," *Br. J. Cardiol. (Acute & Interventional Cardiology)*, 2004, 11: AIC80-AIC84.
Grube, "Bioabsorbable Stents—The Boston Scientific & REVA Technology," *EuroPCR 2009*, 2009, pp. 1-27.
Gu et al., "In vitro Corrosion and biocompatibility of binary magnesium alloys," *Biomaterials*, vol. 30, 2009, pp. 484-498.
Gupta et al., "Nanometer spaced electrodes using selective area atomic layer deposition," *Applied Physics Letters*, vol. 90, 2007, pp. 1-4.
Haenzi et al., "Design strategy for microalloyed ultra-ductile Mg alloys," *Phil. Mag. Letters*, 89(6): 377-390.
Haenzi et al., "Design strategy for new biodegradable Mg—Y—Zn alloys for medical applications," *Int. J. Mat. Res.*, 2009, 100: 1127-1136.
Haenzi et al., "On the biodegradation performance of an Mg—Y—Re alloy with various surface conditions in simulated body fluid," *Acto Biomat.*, 2009, 5: 162-171.
Hamu et al., "Influence of Si, Ca and Ag addition on corrosion behavior of new wrought Mg—Zn alloys," 2006, 22(10): 1213-1218.
Hänzi et al., "Design strategy for microalloyed ultra-ductile magnesium alloys," *Philosophical Magazine letters*, vol. 89, No. 6, Jun. 2009, pp. 377-390.
Hänzi et al., "Design strategy for new biodegradable Mg—Y—Zn alloys for medical applications," *Int. J. Mat. Res.*, vol. 100, 2009, pp. 1127-1136.
Hänzi et al., "On the biodegradation performance of an Mg—Y—Re alloy with various surface conditions in simulated body fluid," *Acta Biomaterialia*, vol. 5, 2009, pp. 162-171.

Haque et al. "Bioabsorption Qualities of Chitosan-absorbable Vascular Templates," *Current Surgery*, 2001, 58(1): 77-80.
Heismann et al., "Density and atomic number measurements with spectral x-ray attenuation method," *Journal of Applied Physics*, vol. 94, No. 3, Aug. 1, 2003, pp. 2073-2079.
Hermawan et al., "Developments in metallic biodegradable stents," *Acta Biomaterialia*, 2010, 6: 1693-1697.
Hermawan et al., "Degradable metallic biomaterials: Design and development of Fe—Mn alloys for stents," *Wiley InterScience: Article*, Apr. 19, 2008, pp. 1-12.
Hermawan et al., "Degradation Behaviour of Metallic Biomaterials for Degradable Stents," *Advanced Materials Research*, 2007, 15-17:113-118.
Hermawan et al., "Development of Degradable Fe-35Mn Alloy for Biomedical Application," *Advanced Material Research*, 2007, 15-17:107-112.
Hermawan et al., "Fe—Mn Alloys for Metallic Biodegradable Stents: Degradation and Cell Viability Studies," *Acta Biomaterialia*, Manuscript, Mar. 27, 2009, pp. 1-30.
Hermawan, et al., "Iron-Manganese: new class of metallic degradable biomaterials prepared by powder metallurgy," *Powder Metallurgy*, 2008, 51(1):38-45.
Hildebrandt et al., "Prevention of surface encrustation of urological implants by coating with inhibitors," *Biomaterials*, 2001, 22:503-507.
Holclajtner-Antunovic et al., "Study of some polyoxometallates of Keggin's type as potention antitumour agents," *Jugoslov Med. Biohem.*, 2004, 23: 25-30.
Hourng et al., Influence of multisteps thermal control in metal powder injection moulding process, *Powder Metallurgy*, 2008, 51: 84-89.
Hutten, A. et al. "Ferromagnetic FeCo nanoparticles for biotechnology". (2005) *Journal of Magnetism and Magnetic Materials* 293:93-101).
Iakovou et al., "Incidence, Predictors, and Outcome of Thrombosis Successful Implantation of Drug-Eluting Stents," *JAMA*, 2005, 293(17): 2126-2130.
Ignat et al., "Magnesium alloys (WE43 and ZE41) characterization for laser applications," *Applied Surface Science*, 2004, 233:382-391.
Iida et al. "Surface modification of of $\lambda Fe_2O_3$ nanoparticles with aminopropylsilyl groups and interparticle linkage with with a,w-Dicarboxylic Acids", *Electrochima Acta*. 2005. 855-859.
Imgrund, "Evaluation of metal injection moulding (MIM) and extrusion as processing technology for biodegradable stents. A 208143: Final report for phase I MIM of Fe—Si powders and sample characterisation," Aug. 15, 2008, *Fraunhofer Institut Fertigungstechnik Material forschung*, 18 pages.
Integran, "Biodegradable Nanometallic Intracoronary Stents," May 12, 2009, 1 page.
Integran, "Biodegradable Nanometallic Intracoronary Stents," Proposal, May 12, 2009, 1 page.
International Preliminary Report on Patentability received in PCT/US2007/078479, mailed Mar. 26, 2009, 8 pages.
International Search Report / Written Opinion in PCT/US09/046750 mailed Jul. 20, 2010, 14 pages.
International Search Report and Written Opinion received in PCT/US2007/078417, mailed Jan. 22, 2009, 18 pages.
International Search Report and Written Opinion received in PCT/US2007/078479, mailed Dec. 30, 2008, 12 pages.
International Search Report from PCT/US 03/20215, mailed Nov. 11, 2003, 4 pages.
International Search Report/Written Opinion in PCT/US2007/078407, mailed Mar. 26, 2008, 10 pages.
Jabara et al., "Bioabsorbable Stents: The Future is Near," *Cardiac Interventions Today*, Jun./Jul. 2009, pp. 50-53.
Jabara, "Poly-anhydride based on salicylic acid and adipic acid anhydride," Glimpse into the future: bioabsorbable stents-aimint to restore vascular integrity, *Euro PCR09*, 2009, pp. 1-34.
James A. Plambeck, "Electrolytic Processes of Nonmetals," *Chemical Sciences*, 1995, 2 pages.
Jiang et al., "Corrosion protection of polypyrrole electrodeposited on AZ91 magnesium alloys in alkaline solutions," *Synthetic Materials*, 2003, 139: 335-339.

(56) References Cited

OTHER PUBLICATIONS

Jiang et al., "Effect of TiB$_2$ particulate on partial remelting behavior of Mg-11A1-0.5Zn matrix composite," *Materials Science and Engineering A*, 2004, 381: 223-229.

Kaesel et al., "Approach to Control the Corrosion of Magnesium by Alloying," *Magnesium Proceedings of the 6$^{th}$ International Conference Magnesium Alloys and Their Applications*, 2004, pp. 534-539.

Kainer, "Magnesium alloys and technology," Wiley VCH, 2003, 119 pages.

Kaya et al., "Microstructure and Corrosion Resistance of Alloys of the Mg—Zn—Ag System," *Metal Science and Heat Treatment*, 2006, 48(11-12): 524-530.

Kececioglu, "Zur Biokompatibilitat eines neu entwickelten Stentmaterials aus korrodierbarem Reineisen," Jan. 25, 2007, pp. 1-131, *Ruhr-Universitat-Bochum*.

Kidambi et al., "Selective depositions on polyelectrolyte multilayers: self-assembled monolayers of m-dPEG acid as molecular template," *J. Am. Chem. Soc.*, 2004, 126: 4697-4703.

Kokubo et al., "How useful is SBF in predicting in vivo bone bioactivity?" *Biomaterials*, 2006, 27: 2907-2915.

LaFont, "Arterial Remodeling Technologies: Bioresorbable Stents," *EURO PCR09*, 2009, pp. 1-28.

Lee, J. et al. "Simple synthesis of mesoporous carbon with magnetic nano particles embedded in carbon rods". (2005) Carbon 43:2536-2543.

Lee, Sang-Yup et al. "Surface modification of magnetic nanoparticles capped by oleic acids: Characterization and colloidal stability in polar solvents" *Journal of Colloid and Interface Science* 293 (2006) 401-408.

Levesque et al., "Design of pseudo-physiological test bench specific to the development of biodegradable metallic biomaterials," *Acta Biomaterialia*, 2008, 4:284-295.

Li et al., "Effects of Direct Current on Dog Liver: Possible Mechanisms for Tumor Electrochemical Treatment," *Bioelectromagnetics*, 1997, 18:2-7.

Li et al., "Photoacoustic Tomography and Sensing in Biomedicine," *Phys. Med. Biol.*, 2009, 54:59-97.

Li, "Poly(L-glutamic acid)-anticancer drug conjugates," *Advanced Drug Delivery Reviews*, 2002, 54: 695-713.

Liu et al., "Characterizations of polypyrrole (PPy) nano-tubules made by templated ac electropolymerization," *European Polymer Journal*, 2005, 41: 2117-2121.

Lu et al. "Magnetic Switch of Permeability for Polyelectrolyte Microcapsules Embedded with Co@Au Nanoparticles". *American Chemical Society*. 2004.

Lu et al., "Theoretical analysis of calcium phosphate precipitation in simulated body fluid," *Biomaterials*, 2005, 26:1097-1108.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.

Maendl, "Zerstaubungsabscheidung von Mg-Legierungen," *Leibniz-Institut fur Oberflachenmodifizierung*, 2001, pp. 1-17.

Mani et al., "Coronary Stents: A materials perspective," *Biomaterials*, 2007, 28:1689-1710.

Mansfeld, Florian. "Analysis and Interpretation of EIS Data for Metals and Alloys," *Solartron Analytical*, 1999, 1-77.

Marijan et al. "Surface Modification of Stainless Steel-304 Electrode. 2. An Experimental Comparative Study of Electrochemically, Hydrothermally and Chemically Modified Oxide Films." *CCACAA*, 1999, 72(4) 751-761.

Markman, "Absorbable Coronary stents," *The Lancet*, Jun. 2, 2007, 369:1839-1840.

Massaro et al., "Comparative Investigation of the surface properties of commercial titanium dental implants. Part 1: chemical composition," *Journal of Materials Science: Materials in Medicine*, vol. 13, 2002, pp. 535-548.

Meng Han, "Laser nitriding of metals: Influences of the ambient pressure and the pulse duration," 2001, Dissertation, Georg-August-Universität Göttingen, 134 pages.

Miao et al., "Porous Calcium Phosphate Ceramics prepared by coating polyurethane foams with Calcium phosphate cements," *Materials Letters*, vol. 58, 2004, pp. 397-402.

Mueller et al., "Control of smooth muscle cell proliferation by ferrous iron," *Biomaterials*, vol. 27, 2006, pp. 2193-2200.

Mueller et al., "Magnesium and its Alloys as Degradable Biomaterials, Corrosion Studies Using Potentiodynamic and EIS Electrochemical Tenchiques," *Materials Research*, 2007, 10(1): 5-10.

Mueller et al., "Preparation of SBF with different HCO$_3$ content and its influence on the composition of biomimetic apatites," *Acta Biomaterialia*, 2006, 2:181-189.

Munoz et al., "Interactive Effects of Albumin and Phosphate Ions on the Corrosion of CoCrMo Implant Alloy," *Journal of the Electrochemical Society*, 2007, 154(10):562-570.

Nachtrab et al., "Quantitative Material Analysis by Dual-Energy Computed Tomography for Industrial NDT Applications," *Fraunhofer EZRT*, date unknown, 1 page.

Nair and Laurencin, "Biodegradable polymers as biomaterials," *Prog. Polym. Sci.*, 2007, 32: 762-798.

Nguyen et al., "Mechanism for protection of iron corrosion by an intrinsically electronic conducting polymer," *Journal of Electroanalytical Chemistry*, 2004, 572: 225-234.

Ni et al., "Cellular localization of antiviral polyoxometalates in J774 macrophages," *Antiviral Research*, 1995, 32: 141-148.

Niinisto, "Atomic Layer deposition: A key technology for the controlled growth of oxide thin films for advanced applications," *Proc. Estonian Acad. Sci. Phys. Math.*, 2003, 52(3):266-276.

Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.

Onuma et al., "Everolimus-eluting bioabsorbable stent," *Euro PCR09*, May 22, 2009, pp. 1-28.

Ormiston et al., "Bioabsorbable Coronary Stents," *Circulation Cardiovasc Intervent*, vol. 2, 2009, pp. 255-260.

Ouerd et al., "Reactivity of Titanium in Physiolgoical Medium—I. Electrochemical Characterization of the Metal/Protein Interface," *Journal of the Electrochemical Society*, vol. 154, No. 10, 2007, pp. 593-601.

Oyane et al., "Preparation and assessment of revised simulated body fluids," *Wiley Periodicals, Inc.*, 2003, pp. 188-195.

Paliwoda-Porebska et al., "On the development of polypyrrole coatings with self-healing properties for iron corrosion protection," *Corrosion Science*, 2005, 47: 3216-3233.

Peeters et al., "Preliminary Results after Application of Absorbable Metal Stents in Patients with Critical Limb Ischemia," *J. Endovasc Ther*, 2005, 12:1-5.

Peeters, et al., "Preliminary Data on Absorbable Metal Stents," *MEET 2006*, Jun. 2006, pp. 1-30.

Peuster et al., "Are resorbable implants about to become a reality," *Cardiol Young*, 2006, 16:107-116.

Pinto Slattow et al., "Optical coherence tomography and intravascular ultrasound imaging of bioabsorbable magnesium stent degradation in porcine coronary arteries," *Cardiovascular Revascularization Medicine* 9, (2008) pp. 248-254.

Purushothaman et al. "Reducing Mass-Transport Limitations by Application of Special Pulsed Current Modes". *Journal of the Electrochemical Society*. 152 (4), 2005, J33-J39.

Qasem et al., "Kinetics of paclitaxel 2'-N-methylpyridinium mesylate decomposition," *AAPS PharmSciTech*, 2003, 4(2), Article 21, 8 pages.

Quinard et al., "Development of metal/polymer mixtures for micro powder injection moulding," *10th ESAFORM Conference on Material Forming*, 2007, pp. 933-939.

Qureshi et al., "The emerging role of iron, zinc, copper, magnesium and selenium and oxidative stress in health and diseases," *Biogenic Amines*, vol. 19, No. 2, 2005, pp. 147-169.

Raman et al., "Laser assisted modification of surface microstructure for localised corrosion resistance of magnesium alloys," *Surface Engineering*, 2007, 23(2): 107-111.

Reece et al., "Metal transport studies on inherently conducting polymer membrances containing cyclodextrin dopants," *Journal of Membrane Science*, 2005, 249: 9-20.

(56) References Cited

OTHER PUBLICATIONS

Ren et al., "Variations of dose and electrode spacing for rat breast cancer electrochemical treatment," *Bioelectromagnetics*, 2001, 22(3):205-211.

Rettig et al., "Composition of corrosion layers on a magnesium rare-earth alloy in simulated body fluids," *Journal of Biomedical Materials Research Part A*, Oct. 18, 2006, pp. 359-369.

Rettig et al., "Corrosion resistance studies on grain-boundary etched drug-eluting stents," *J. Mater Sci: Mater Med.*, 2007, vol. 18, pp. 1377-1387.

Rettig et al., "Time-dependent electrochemical characterization of the corrosion of a magnesium rare-earth alloy in simulated body fluids," *Journal of Biomedical Materials Research Part A*, 2007, 167-175.

Rinkevich et al., "Regeneration of Amputated Avian Bone by a Coral Skeletal Implant," *Biol. Bull.*, vol. 197, Aug. 1999, pp. 11-13.

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Schauer et al., "Protection of iron against corrosion with polyaniline primers," *Progress in Organic Coatings*, 1998, 33: 20-27.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geological Society of London*, Paper 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pp. 671-673.

Secheresse et al., "$(Mo_2O_2X_2)^{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity—Introduction & Objectives," *Euro PCR09*, May 18, 2009, pp. 1-4.

Shevchenk et al., "Porous Surface of NiTi Alloy Produced by Plasma Ion Implantation," *Institute of Ion Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shieh et al. "Aqueous dispersions of magnetic nanoparticles with NH3 surfaces for magnetic manipulations of biomolecules and MRI contrast agents" *Biomaterials*, 2005 26: 7183-7191.

Sieber, et al., "Investigations on the passivity of iron in borate and phosphate buffers, pH 8.4," *Corrosion Science*, vol. 48, 2006, pp. 3472-3488.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science*. 2004. 75:1-68.

Soto et al., "Amorphous magnesium nitride films produced by reactive pulsed lasar deposition," Journal of Non-Crystalline Solids, 2004, 342: 65-69.

Stoner et al., "The mechanism of low frequency a.c. Electrochemical Disinfection," *Bioelectrochemistry and Bioenergetics*, 1982, 9:229-243.

Su et al., "Photoacoustic imaging of coronary artery stents," *Optics Express*, vol. 17, No. 22, Oct. 26, 2009, pp. 1-8.

Sun et al., "Fabrication of a multilayer film electrode containing porphyrin and its application as a potentiometric sensor of iodide ion," *Talanta*, 1998, 46: 15-21.

Truong et al., "Corrosion protection of magnesium by electroactive polypyrrole/paint coatings," *Synthetic Metals*, 2000, 110: 7-15.

Turler et al., "Experimental low-level direct current therapy in liver metastases: influence of polarity and current dose," *Bioelectromagnetics*, 2000, 21(5):395-401.

Uhlmann et al., "Schnelle 3D-Analyse von Gefugemerkmalen" *Druckguss*, Apr. 2009, pp. 1-5.

Van Alst, "Potential conflicts of interest," *Euro PCR09*, 2009, pp. 1-22.

Virtanen et al., "Electrochemical Behavior of Fe in Phosphate Solutions Studied by In Situ X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, Nos. 2-3, 2008, pp. 147-171.

Volkova, "Effect of Deformation and Heat Treatment on the Structure and Properties of Magnesium Alloys of the Mg—Zn—Zr System," *Metal Science and Heat Treatment*, vol. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

Waksman et al., "Early- and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro PCR09*, 2009, pp. 1-24.

Waksman, Ron, "Why Bioabsorbale Stent Technology," Glimpse to the Future, *Euro PCR09*, 2009, pp. 1-16.

Wan et al., "Preparation and characterization of porous conducting poly(DL-lactide) composite membranes," *Journal of Membrane Science*, 2005, 246: 193-201.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices," J. Polymer Science, Part A: Polymer Chemistry, 2004, 42: 1658-1667.

White and Slade, "Polymer electrodes doped with heterpolymetallates and their use within solid-state supercapacitors," *Synthetic Metals*, 2003, 139: 123-131.

Wilcox, "Biodegradable Technology: Medtronic Biodegradable Stent Program," *Euro PCR09*, 2009, pp. 1-25.

Windecker et al., "Biolimus-eluting stent with biodegradable polymer versus sirolimus-eluting stent with durable polymer for coronary revascularisations (LEADRERS): a randomized non-inferiority trial," *The Lancet*, Sep. 1, 2008, pp. 1-11.

Witte et al., "Biodegradable magnesium-hydroxyapatite metal matrix composites," *Biomaterials*, vol. 28, 2007, pp. 2163-2174.

Witte et al., "In Vivo Corrosion of Four Magnesium Alloys and the Associated Bone Response," *Biomaterials*, vol. 26, 2005, pp. 3557-3563.

(56) References Cited

OTHER PUBLICATIONS

Witte, "The history of biodegradable magnesium implants: A review," *Acta Biomaterialia*, 2010, 6: 1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation of spinal cages," *Eur. Spine J.*, 2006, 15: 133-148.

Xin et al., "Electrochemical Treatment of Lung Cancer," *Bioelectromagnetics*, 1997, 18:8-13.

Xu et al., "In Vivo corrosion behaviouc of Mg—MnZn alloy for bone implant application," *Journal of Biomedical Materials Research Part A*, Jun. 4, 2007, pp. 703-711.

Ye et al., "In situ synthesis of AlN particles in Mg—Al alloy by $Mg_3$—$N_2$ addition," *Materials Letters*, 2004, 58: 2361-2361.

Yen et al., "Electrochemical treatment of human KB cells in vitro," *Bioelectromagnetics*, 1999, 20:34-41.

Yfantis et al., "Novel corrosion-resistant films for Mg alloys," *Surface and Coatings Technology*, 2002, 151-152: 400-404.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

Zheng, "Symposium on Biodegradable/Biocorroded metallic materials," Nov. 24, 2009, pp. 1-74.

Zhu et al., "Biocompatibility of Fe—O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation kinetics and cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}{}_{62}$ doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

International Search Report and Written Opinion from PCT/US09/043591, mailed Jun. 30, 2010, 10 pages.

International Search Report from PCT/US07/005671, mailed Jun. 2, 2008, 10 pages.

Ma et al., "Inhibition effect of self-assembled films formed by gold nonoparticles on iron surface," *Applied Surface Science*, 2006, 252: 4327-4334.

Li et al., "The corrosion inhibition of the self assembled Au, and Ag nonoparticles films on the surface of copper," *Colloids and Surfaces A: Physiochem. Eng. Aspects*, 2006, 273: 16-23.

International Preliminary Report on Patentability from PCT/US08/75976 dated Mar. 25, 2010, mailed Nov. 25, 2008, 8 pages.

\* cited by examiner

BIOERODIBLE ENDOPROSTHESES AND METHODS OF MAKING THE SAME

TECHNICAL FIELD

The invention relates to bioerodible endoprostheses, and to methods of making the same.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, e.g., so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn from the lumen.

It is sometimes desirable for an implanted endoprosthesis to erode over time within the passageway. For example, a fully erodible endoprosthesis does not remain as a permanent object in the body, which may help the passageway recover to its natural condition. Erodible endoprostheses can be formed from, e.g., a polymeric material, such as polylactic acid, or from a metallic material, such as magnesium, iron or an alloy thereof.

SUMMARY

The invention relates to bioerodible endoprostheses and methods of making the endoprostheses. The endoprostheses can be configured to erode in a controlled and predetermined manner in the body.

In one aspect, the invention features an endoprosthesis that includes a first metallic portion having a first erosion rate, and a second metallic portion having a second erosion rate different from the first erosion rate.

The first and second metallic portions can, e.g., include a common metal, e.g., magnesium, calcium, zinc or iron. In some instances, at least one of the metallic portions is substantially a pure metal. In some embodiments, the first metallic portion includes an outside surface or an inside surface of the endoprosthesis, and the second metallic portion is disposed inwardly of the first portion. The first and second metallic portions can be, e.g., circular in a transverse cross-section. One of the metallic portions can be, e.g., formed from a metallic alloy.

In some embodiments, a thickness of the metallic portion having a lower erosion rate is from about 10 nm to about 1000 nm, e.g., from about 15 nm to about 100 nm.

The erosion rate of the metallic portion having a lower erosion rate can be, e.g., from about 0.01 percent of an initial mass of that portion per day to about 1 percent of the initial mass of that portion per day, e.g., from about 0.1 percent of the initial mass of that portion per day to about 0.5 percent of the initial mass of that portion per day.

The erosion rate of the metallic portion having a higher erosion rate can be, e.g., from about 0.2 percent of an initial mass of that portion per day to about 10 percent of the initial mass of that portion per day, e.g., from about 0.5 percent of the initial mass of that portion per day to about 5 percent of the initial mass of that portion per day.

The erosion rate of the metallic portion having the higher erosion rate can be, e.g., from about ten percent to about one-hundred percent greater than the erosion rate of the metallic portion having the lower erosion rate.

In some embodiments, the first and second metallic portions are disposed within a longitudinal segment of the endoprosthesis. The endoprosthesis can include a plurality of segments, e.g., arranged along a longitudinal length of the endoprosthesis.

In some embodiments, the endoprosthesis is adapted to erode sequentially along a longitudinal length of the endoprosthesis, e.g., in a direction transverse to the longitudinal length of the endoprosthesis.

In some embodiments, the endoprosthesis includes an inner surface, an outer surface, and a portion between the inner and outer surfaces. The portion between the inner and outer surfaces has an erosion rate higher than an erosion rate of the inner surface or the outer surface.

In some embodiments, the endoprosthesis is tubular in form.

The endoprosthesis car, e.g., include a stent.

In another aspect, the invention features a method of making an endoprosthesis that includes implanting a material into a first portion of an erodible endoprosthesis. The implanted first portion has a higher concentration of the first material than a second portion of the endoprosthesis. In some embodiments, the first portion has a different erosion rate than the second portion. The implanted material can include, e.g., nitrogen, carbon, silicon, oxygen, sulfur, chromium, silver, gold, boron, or mixtures of these elements. The erodible endoprosthesis can include, e.g., magnesium, calcium, lithium, rare earth elements, iron, aluminum, zinc, manganese, cobalt, copper, zirconium, titanium, or mixtures of these elements.

In some embodiments, the implanting employs a plasma.

In some embodiments, the method further includes, prior to implanting, applying a shielding, e.g., a coating, e.g., a polymeric coating, to a portion of the endoprosthesis. In some embodiments, after applying the shielding, the method further includes removing the applied shielding.

Aspects and/or embodiments may have one or more of the following advantages. The endoprostheses may not need to be removed from a lumen after implantation. The endoprostheses can have a low thrombogenecity and high initial strength. The endoprostheses can exhibit reduced spring back (recoil) after expansion. Lumens implanted with the endoprostheses can exhibit reduced restenosis. The rate of erosion of different portions of the endoprostheses can be controlled, allowing the endoprostheses to erode in a predetermined manner, reducing, e.g., the likelihood of uncontrolled fragmentation. For example, the predetermined manner of erosion can be from an inside of the endoprosthesis to an outside of the endoprosthesis, or from a first end of the endoprosthesis to a second end of the endoprosthesis.

An erodible or bioerodible endoprosthesis, e.g., a stent, refers to an endoprosthesis, or a portion thereof, that exhibits substantial mass or density reduction or chemical transformation, after it is introduced into a patient, e.g., a human patient. Mass reduction can occur by, e.g., dissolution of the material that forms the endoprosthesis and/or fragmenting of the endoprosthesis. Chemical transformation can include oxidation/reduction, hydrolysis, substitution, and/or addition reactions, or other chemical reactions of the material from which the endoprosthesis, or a portion thereof, is made. The erosion can be the result of a chemical and/or biological interaction of the endoprosthesis with the body environment, e.g., the body itself or body fluids, into which it is implanted and/or erosion can be triggered by applying a triggering influence, such as a chemical reactant or energy to the endoprosthesis, e.g., to increase a reaction rate. For example, an endoprosthesis, or a portion thereof, can be formed from an active metal, e.g., Mg or Ca or an alloy thereof, and which can erode by reaction with water, producing the corresponding metal oxide and hydrogen gas (a redox reaction). For example, an endoprosthesis, or a portion thereof, can be formed from an erodible or bioerodible polymer, or an alloy or blend erodible or bioerodible polymers which can erode by hydrolysis with water. The erosion occurs to a desirable extent in a time frame that can provide a therapeutic benefit. For example, in embodiments, the endoprosthesis exhibits substantial mass reduction after a period of time which a finction of the endoprosthesis, such as support of the lumen wall or drug delivery is no longer needed or desirable. In particular embodiments, the endoprosthesis exhibits a mass reduction of about 10 percent or more, e.g. about 50 percent or more, after a period of implantation of one day or more, e.g. about 60 days or more, about 180 days or more, about 600 days or more, or 1000 days or less. In embodiments, the endoprosthesis exhibits fragmentation by erosion processes. The fragmentation occurs as, e.g., some regions of the endoprosthesis erode more rapidly than other regions. The faster eroding regions become weakened by more quickly eroding through the body of the endoprosthesis and fragment from the slower eroding regions. The faster eroding and slower eroding regions may be random or predefined. For example, faster eroding regions may be predefined by treating the regions to enhance chemical reactivity of the regions. Alternatively, regions may be treated to reduce erosion rates, e.g., by using coatings. In embodiments, only portions of the endoprosthesis exhibits erodibilty. For example, an exterior layer or coating may be erodible, while an interior layer or body is non-erodible. In embodiments, the endoprosthesis is formed from an erodible material dispersed within a non-erodible material such that after erosion, the endoprosthesis has increased porosity by erosion of the erodible material.

Erosion rates can be measured with a test endoprosthesis suspended in a stream of Ringer's solution flowing at a rate of 0.2 m/second. During testing, all surfaces of the test endoprosthesis can be exposed to the stream. For the purposes of this disclosure, Ringer's solution is a solution of recently boiled distilled water containing 8.6 gram sodium chloride, 0.3 gram potassium chloride, and 0.33 gram calcium chloride per liter.

As used herein, an "alloy" means a substance composed of two or more metals or of a metal and a nonmetal intimately united, for example, by being fused together and dissolving in each other when molten.

All publications, patent applications, patents, and other references mentioned herein are incorporated by reference herein in their entirety.

Other aspects, features, and advantages will be apparent from the description and drawings, and from the claims.

DETAILED DESCRIPTION

Figure 1A:
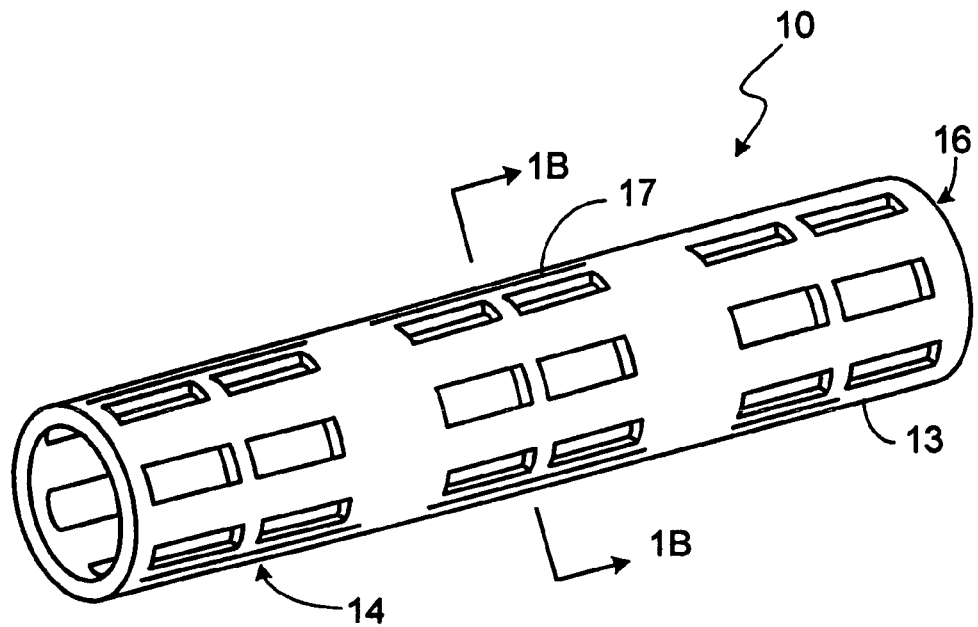
FIG. 1A is a perspective view of an embodiment of an erodible stent.
Figure 1B:
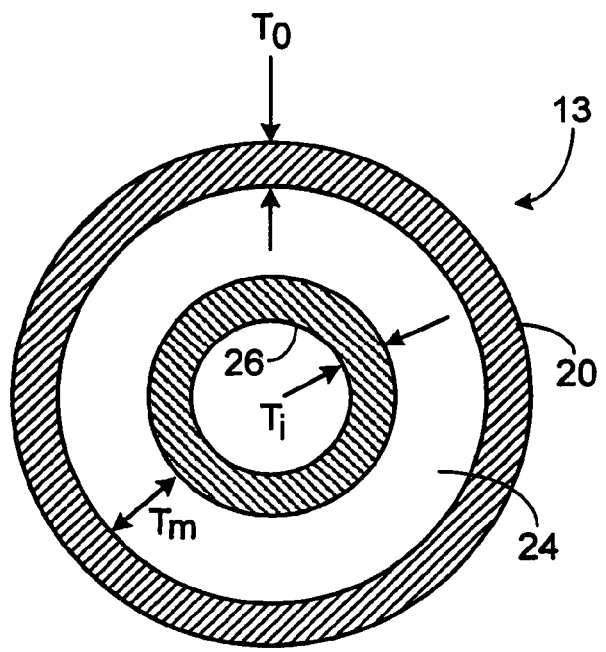
FIG. 1B is a cross-sectional view of the stent of FIG. 1A, taken along line 1B-1B.

FIGS. 1A and 1B show an erodible stent 10 configured to erode in a controlled and predetermined manner. As shown, stent 10 includes a tubular body 13 having an outer portion 20, an inner portion 26, and middle portion 24 between the outer and inner portions. Middle portion 24 has a first metallic composition, such as an erodible magnesium alloy, that has a first erosion rate. Outer and inner portions 20, 26 have a second metallic composition that has a second erosion rate lower than the first erosion rate. For example, the second composition can include the magnesium alloy of middle portion 24 containing magnesium nitride (e.g., $Mg_3N_2$), which is relatively stable against corrosion and can reduce the erosion rate of the magnesium alloy. Alternatively or additionally, without wishing to be bound by theory, it is believed that the reduction in corrosion can also be due to the densification of the magnesium as a result of nitrogen bombardment (described below). As a result, without changing the bulk mechanical properties of stent 10, outer and inner portions 20, 26 can extend the time it takes the stent to erode to a particular degree of erosion, relative to a stent including the magnesium alloy without the magnesium nitride. This extension of time allows cells of the passageway in which stent 10 is implanted to better endothelialize around the stent, for example, before the stent erodes to a degree where it can no longer structurally maintain the patency of the passageway.

Furthermore, outer and inner portions 20, 26 can be uniform or varied along a direction (e.g., length) of a stent to allow the stent to erode in a predetermined sequence.

Figure 2:
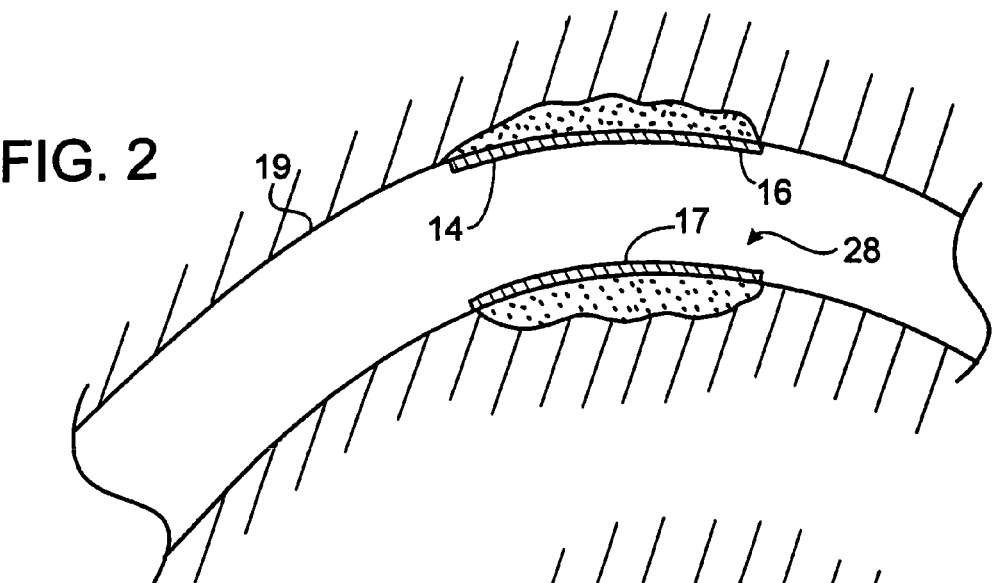
FIGS. 2-4 illustrate erosion of an erodible stent within a body passageway.
Figure 3:
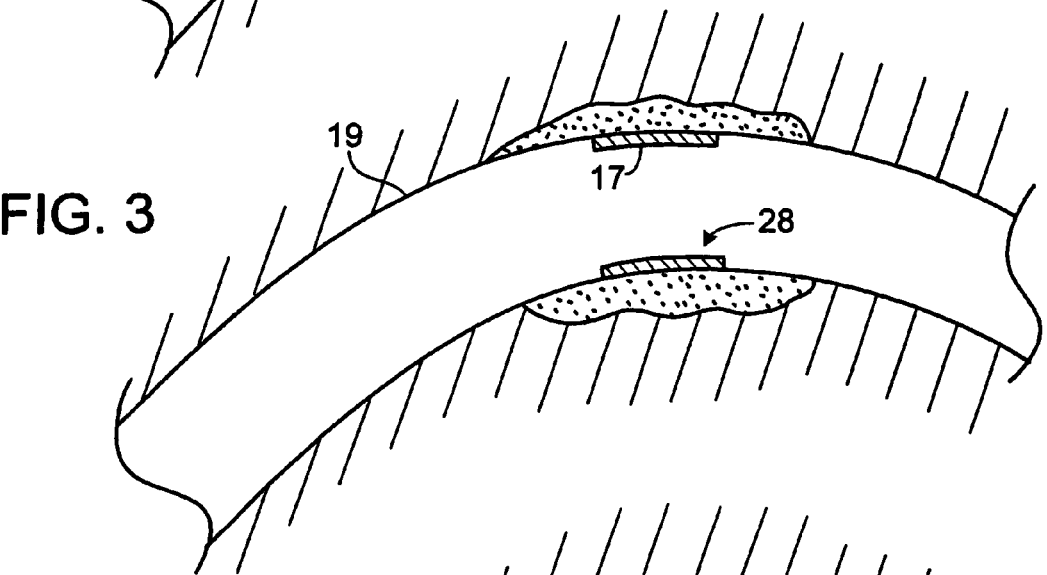
Figure 4:
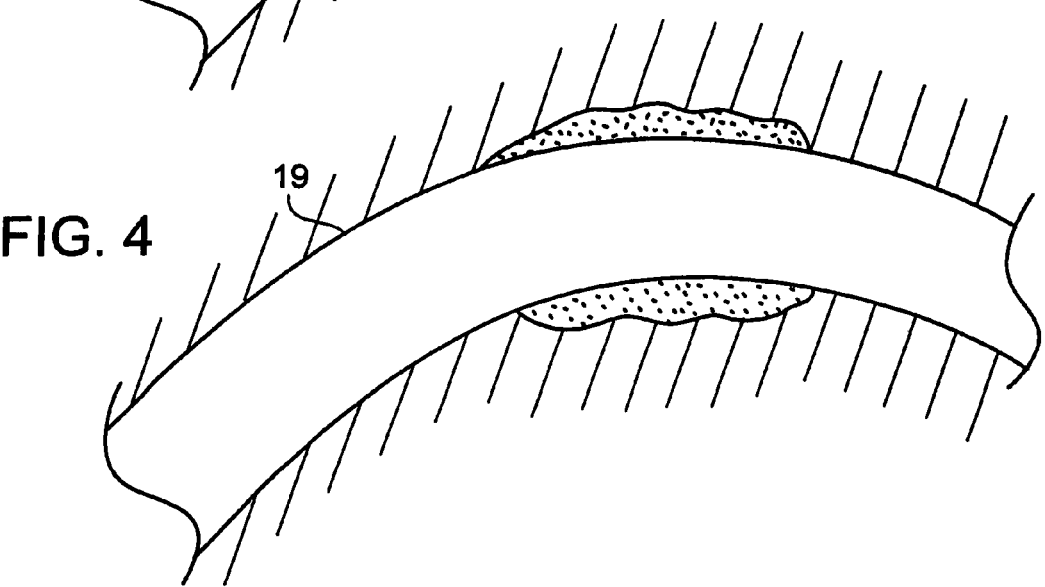

FIGS. 2-4 show a stent 28 implanted in a body vessel 19. Stent 28 is configured to erode progressively from its end portions 14, 16 toward its middle segment 17. For example, outer and inner portions 20, 26 containing magnesium nitride can be relatively thick at middle segment 17 and taper decreasingly in thickness from the middle segment to end portions 14, 16. As a result, end portions 14, 16 can erode before middle segment 17 erodes. This configuration can allow stent 28 to erode in a manner that reduces (e.g., minimizes) the amount of fragments that, if not enveloped by endothelialized cells, may become dislodged and cause complications in the body.

Referring again to FIG. 1B, middle portion 24 of tubular body 13 can include (e.g., be made from) a biocompatible material capable of eroding within the body. The erodible or bioerodible material can be a substantially pure metallic element, or an alloy.

Examples of metallic elements include iron and magnesium. Examples of alloys include iron alloys having, by weight, 88-99.8% iron, 0.1-7% chromium, 0-3.5% nickel, and less than 5% of other elements (e.g., magnesium and/or zinc); or 90-96% iron, 3-6% chromium and 0-3% nickel plus 0-5% other metals. Other examples of alloys include magnesium alloys, such as, by weight, 50-98% magnesium, 0-40% lithium, 0-5% iron and less than 5% other metals or rare earths; or 79-97% magnesium, 2-5% aluminum, 0-12% lithium and 1-4% rare earths (such as cerium, lanthanum, neodymium and/or praseodymium); or 85-91% magnesium, 6-12% lithium, 2% aluminum and 1% rare earths; or 86-97% magnesium, 0-8% lithium, 2% -4% aluminum and 1-2% rare earths; or 8.5-9.5% aluminum, 0.15%-0.4% manganese, 0.45-0.9% zinc and the remainder magnesium; or 4.5-5.3% aluminum, 0.28%-0.5% manganese and the remainder magnesium; or 55-65% magnesium, 30-40% lithium and 0-5% other metals and/or rare earths. Magnesium alloys are also available under the names AZ91D, AM50A, and AE42. Other erodible materials are described in Bolz, U.S. Pat. No. 6,287,332 (e.g., zinc-titanium alloy and sodium-magnesium alloys); Heublein, U.S. Patent Application 2002000406; and Park, *Science and Technology of Advanced Materials,* 2, 73-78 (2001), all of which are hereby incorporated by reference herein in their entirety. In particular, Park describes Mg—X—Ca alloys, e.g., Mg—Al—Si—Ca, Mg—Zn—Ca alloys.

Outer and inner portions 20, 26 of tubular body 13 can include a erodible combination of the erodible material of middle portion 24 and one or more first materials capable of reducing the erosion rate of the erodible material. In some embodiments, the erosion rate of outer and inner portions 20, 26 is from about 10% to about 300% less than the erosion rate of middle portion 24, for example, from about 25% to about 200% less, or from about 50% to about 150% less. The erosion rate of outer and inner portions 20, 26 can range from about 0.01 percent of an initial mass of that portion per day to about 1 percent of the initial mass of that portion per day, e.g., from about 0.1 percent of the initial mass of that portion per day to about 0.5 percent of the initial mass of that portion per day. The erosion rate of middle portion 24 can range from about 0.2 percent of an initial mass of that portion per day to about 10 percent of the initial mass of that portion per day., e.g., from about 0.5 percent of the initial mass of that portion per day to about 5 percent of the initial mass of that portion per day. Examples of first materials include magnesium nitride, magnesium oxide, magnesium fluoride, iron nitride and iron carbide. Iron nitride and iron carbide materials are discussed in Weber, *Materials Science and Engineering,* A199, 205-210 (1995), and magnesium nitride is discussed in Tian, Surface and Coatings Technology, 198, 454-458 (2005), the entire disclosure of each of which is hereby incorporated by reference herein. Outer and inner portions 20, 26 can have the same chemical composition or different compositions. For example, inner portion 26 may contact bodily fluid more than outer portion 20 (which may contact the wall of the body passageway), and as a result, the inner portion may erode more quickly than the outer portion. To compensate for the difference in erosion and to allow a given cross section of stent 28 to erode relatively uniformly from portions 20, 26 to middle portion 24, the inner portion may have a chemical composition that erodes more slowly than the chemical composition of the outer portion.

The concentration(s) of the first material(s) in outer and inner portions 20, 26 can vary, depending on the desired time to erode through the portions. In embodiments in which the first material(s) reduces the erosion rate of the erodible material, the higher the concentration(s) of the first material(s) in outer and inner portions 20, 26, the more time it takes to erode through the portions. The total concentration of the first material(s) in a portion can range from about 1 percent to about fifty percent. The concentrations of first material(s) in inner portion 26 and outer portion 20 can be the same or different. For example, to compensate for the difference in erosion between portions 20, 26 and to allow a given cross section of stent 28 to erode relatively uniformly from the portions to middle portion 24, the inner portion may have a higher concentration of first material(s) than the outer portion along the cross section.

The thicknesses of outer and inner portions 20, 26 containing the first material(s) can also vary, depending on the desired time to erode through the portions. In embodiments in which the first material(s) reduces the erosion rate of the erodible material, the thicker outer and inner portions 20, 26, the more time it takes to erode through the portions. The thickness of an inner portion or an outer portion including the first material(s) can range from about 1 nm to about 750 nm. The thicknesses of inner portion 26 and outer portion 20 can be the same or different. For example, to compensate for the difference in erosion rates between portions 20, 26 and to allow a cross section of stent 10 to erode relatively uniformly from the portions to middle portion 24, the inner portion may be thicker than the outer portion along the cross section.

The combination of the first material(s) and the erodible material can be formed by plasma treatment, such as plasma immersion ion implantation ("PIII"). During PIII, one or more charged species in a plasma, such as an oxygen and/or a nitrogen plasma, are accelerated at high velocity toward a substrate, such as a stent including the erodible material ("a pre-stent"). Acceleration of the charged species, e.g., particles, of the plasma towards the pre-stent is driven by an electrical potential difference between the plasma and the pre-stent. Alternatively, one could also apply the electrical potential difference between the plasma and an electrode that is underneath the pre-stent such that the stent is in a line-of-sight. Such a configuration can allow part of the pre-stent to be treated, while shielding other parts of the pre-stent. This can allow for treatment of different portions of the pre-stent with different energies and/or ion densities. In some embodiments, the potential difference can be greater than 10,000 volts, e.g., greater than 20,000 volts, greater than 40,000 volts, greater than 50,000 volts , greater than 60,000 volts, greater than 75,000 volts, or even greater than 100,000 volts. Upon impact with the surfaces of the pre-stent, the charged species, due to their high velocity, penetrate a distance into the pre-stent, react with the erodible material, and form stent 10 having portions 20, 26. The penetration depth is being controlled, at least in part, by the potential difference between the plasma and the pre-stent.

Figure 5:
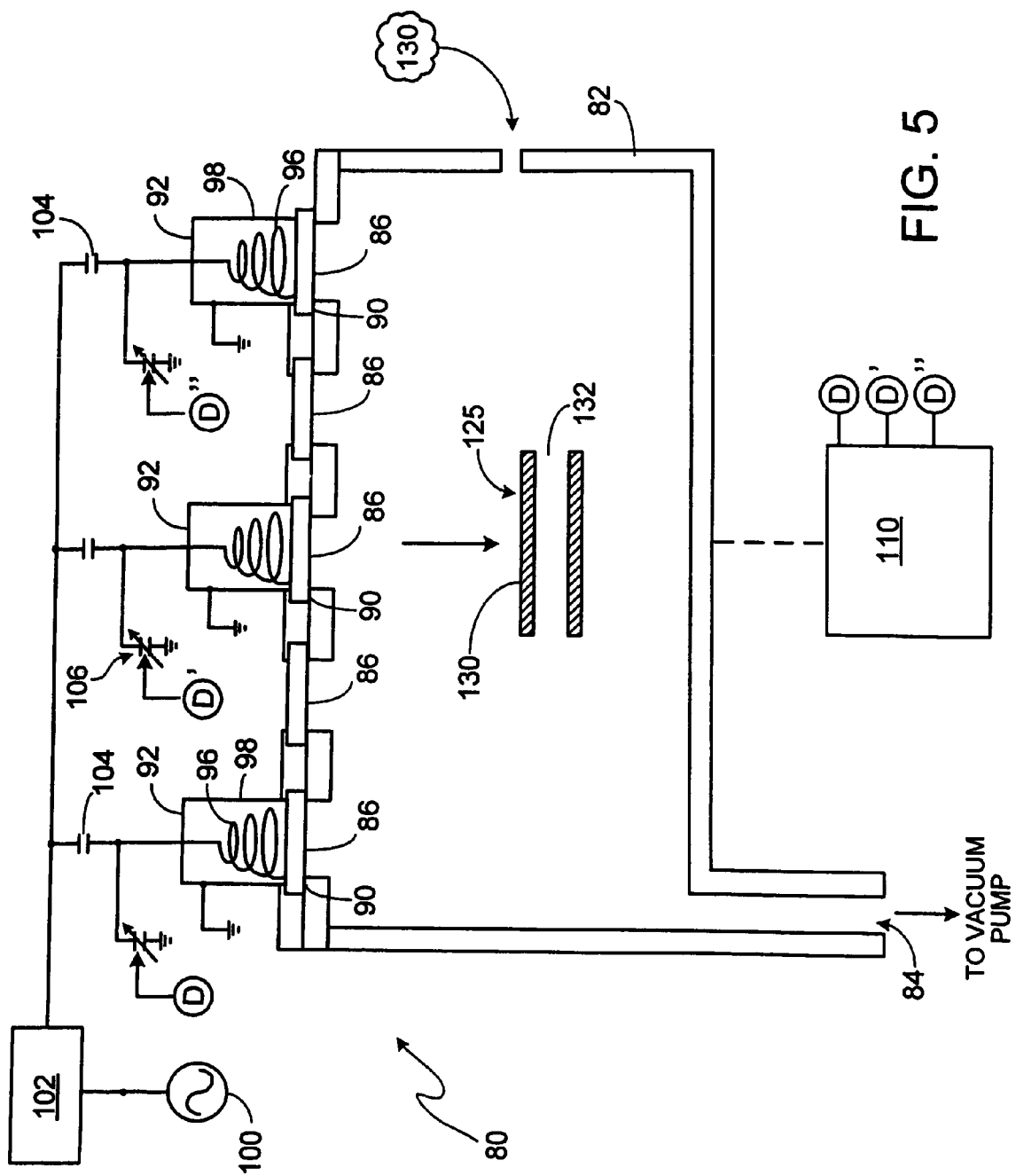
FIG. 5 is a schematic cross-sectional view of a plasma immersion ion implantation ("PIII") system.

FIG. 5 shows an embodiment of a PIII processing system 80. System 80 includes a vacuum chamber 82 having a vacuum port 84 connected to a vacuum pump and a gas source 130 for delivering a gas, e.g., oxygen or nitrogen, to chamber 82 to generate a plasma. System 80 includes a series of dielectric windows 86, e.g., made of glass or quartz, sealed by o-rings 90 to maintain a vacuum in chamber 82. Removably attached to some of the windows 86 are RF plasma sources 92, each source having a helical antenna 96 located within a grounded shield 98. The windows without attached RF plasma sources are usable, e.g., as viewing ports into chamber 82. Each antenna 96 electrically communicates with an RF generator 100 through a network 102 and a coupling capacitor 104. Each antenna 96 also electrically communicates with a tuning capacitor 106. Each tuning capacitor 106 is controlled by a signal D, D', D" from a controller 110. By adjusting each tuning capacitor 106, the output power from each RF antenna 96 can be adjusted to maintain homogeneity of the generated plasma.

In use, a plasma is generated in chamber 82 and accelerated to a pre-stent 125.

Pre-stent 125 can be made, for example, by forming a tube including the erodible material and laser cutting a stent pattern in the tube, or by knitting or weaving a tube from a wire or a filament including the erodible material. A gas, such as oxygen, nitrogen or a silane, is introduced from gas source 130 into chamber 82, where a plasma is generated.

The charged species in the generated plasma, e.g., an oxygen or nitrogen plasma, are accelerated toward all portions of pre-stent 125, including exterior 130 and interior portions 132 of the pre-stent, and thus, become implanted in the pre-stent. PIII has been described by Chu, U.S. Pat. No. 6,120,260; Brukner, *Surface and Coatings Technology*, 103-104, 227-230 (1998); and Kutsenko, *Acta Materialia*, 52, 4329-4335 (2004), the entire disclosure of each of which is hereby incorporated by reference herein.

Ion penetration depth and ion concentration can be modified by changing the configuration of the PIII processing system. For example, when the ions have a relatively low energy, e.g., 10,000 volts or less, penetration depth is relatively shallow when compared with the situation when the ions have a relatively high energy, e.g., greater than 40,000 volts. The dose of ions being applied to a surface can range from about $1 \times 10^4$ ions/cm$^2$ to about $1 \times 10^9$ ions/cm$^2$, e.g., from about $1 \times 10^5$ ions/cm$^2$ to about $1 \times 10^8$ ions/cm$^2$.

Figure 6A:
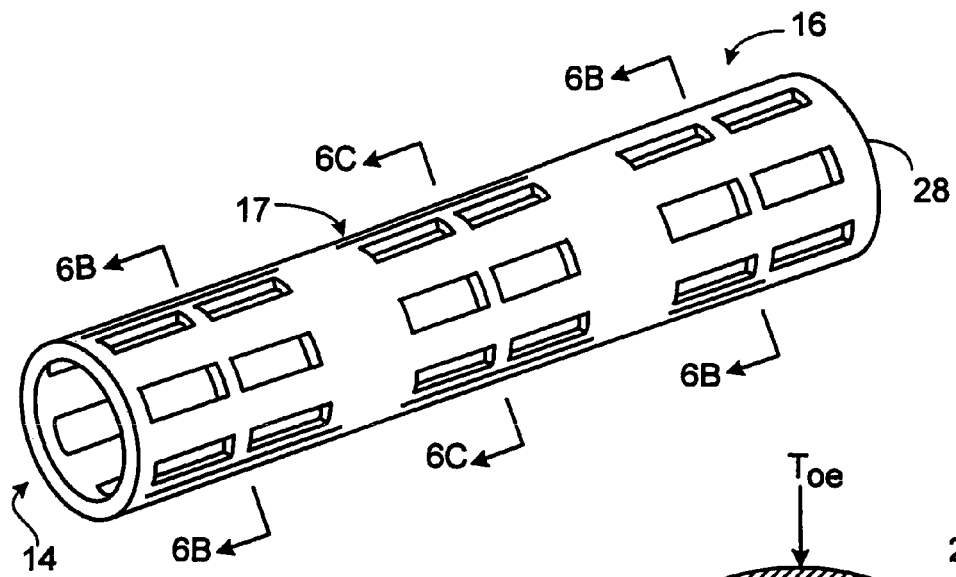
FIG. 6A is a perspective view of an embodiment of an erodible stent.
Figure 6B:
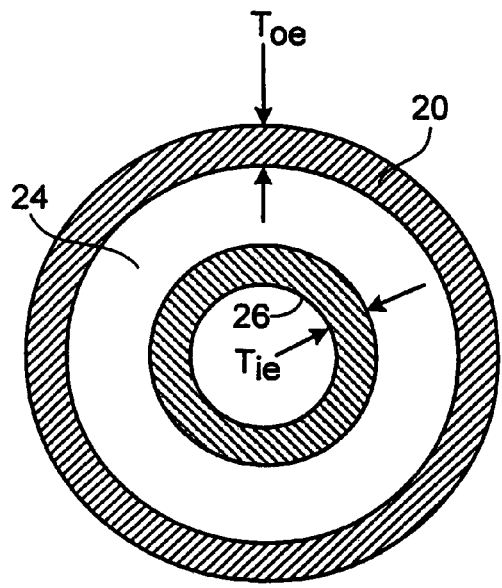
FIG. 6B is a cross-sectional view of the stent of FIG. 6A, taken along line 6B-6B.
Figure 6C:
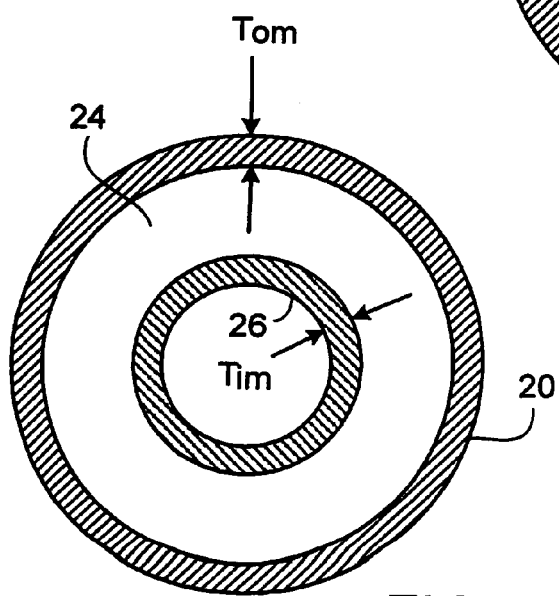
FIG. 6C is a cross-sectional view of the stent of FIG. 6C, taken along line 6C-6C.

In some embodiments, as indicated above, outer and inner portions 20, 26 can be formed non-uniformly (e.g., along the length of a stent) to provide a selected erosion sequence. As shown in FIGS. 2-4, stent 28 can be configured to erode sequentially from its end portions 14, 16 to its middle segment 17 by making the thicknesses of outer and inner portions 20, 26 thinner at the end portions than at the middle segment, in embodiments in which the first material(s) reduces the erosion rate of erodible material. Referring particularly to FIGS. 6A-6C, at end portions 14, 16, the thicknesses of outer and inner portions 20, 26 ($T_{oe}$ and $T_{ie}$) can range from about 1 nm to about 750 nm The thicknesses of outer and inner portions 20, 26 can be the same or different. At middle segment 17, the thicknesses of outer and inner portions 20, 26 ($T_{om}$ and $T_{im}$) can range from about 1 nm to about 750 nm. For each portion 14, 16, 17, the thicknesses of outer and inner portions 20, 26 can be the same or different. Alternatively or additionally to changing the thicknesses of inner and outer portions 20, 26 along stent 28, the chemical composition(s), including the concentration of first material, can be varied along the stent as described above to provide a desired erosion sequence.

For example, in other embodiments, stent 10 can be adapted to erode from a first end to a second end. For example, the thicknesses of outer and inner portions 20, 26 can increase (e.g., in a gradual taper) from end portion 14, along middle segment 17, to end portion 16. As a result, in embodiments in which the first material(s) increases the erosion rate of the erodible material, and the compositions of outer and inner portions 20, 26 are the same along the length of stent 10, the stent can erode sequentially from end portion 14 to end portion 16. Referring to again FIG. 1B, the thickness of outer portion 26 ($T_o$) can range from about 1 nm to about 750 nm, e.g., from about 15 nm to about 500 nm, or from about 15 nm to about 100 nm. The thickness of middle portion 24 ($T_m$) can range from about 0.005 mm to about 2.0 mm, e.g., from about 0.05 mm to about 1.25 mm, or from about 0.05 mm to about 1.0 mm. The thickness of inner portion 26 ($T_i$) can range from about 1 nm to about 750 nm, e.g., from about 15 nm to about 500 nm, or from about 15 nm to about 100 nm.

Figure 7:
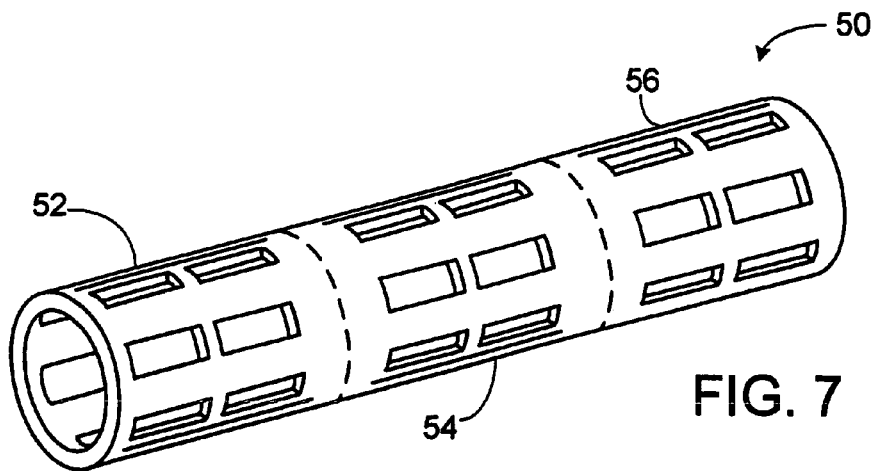
FIG. 7 is a perspective view of an embodiment of an erodible stent.

A stent 10 can also be adapted to erode from a first end to a second end by forming, along the length of the stent, multiple, discrete segments having thicknesses for outer and inner portions 20, 26 that vary in step-wise fashion. Referring to FIG. 7, stent 50 includes three segments 52, 54, 56, each of which has an outer portion and an inner portion including a bioerodible material and one or more first materials. Each segment 52, 54, 56 has an erodible material between its outer and inner surfaces, similar to stent 10. In embodiments in which the first material(s) reduces the erosion rate of the bioerodible material, to erode sequentially from segment 52, to segment 54, to segment 56, the thicknesses of each outer and inner portions can increase from segment 52, to segment 54, to segment 56. For example, the thickness of the inner portion for segment 52 can be 10 nm, the thickness of the inner portion for segment 54 can be 50 nm, and the thickness of the inner portion for segment 56 can be 100 nm. The thicknesses of the inner portions, the outer portions and middle portion can be within the ranges provided above for $T_i$, $T_o$, and $T_m$. In other embodiments, only one of the portions 20, 26 varies along the stent, and the other portion can be constant or taper in thickness. A stent can have two segments, or more than three segments (e.g., four, five, six or more). Alternatively or additionally to varying the thicknesses of outer and inner portions 20, 26, the chemical compositions of the portions can be varied in step-wise fashion to effect a desired erosion sequence.

Figure 8:
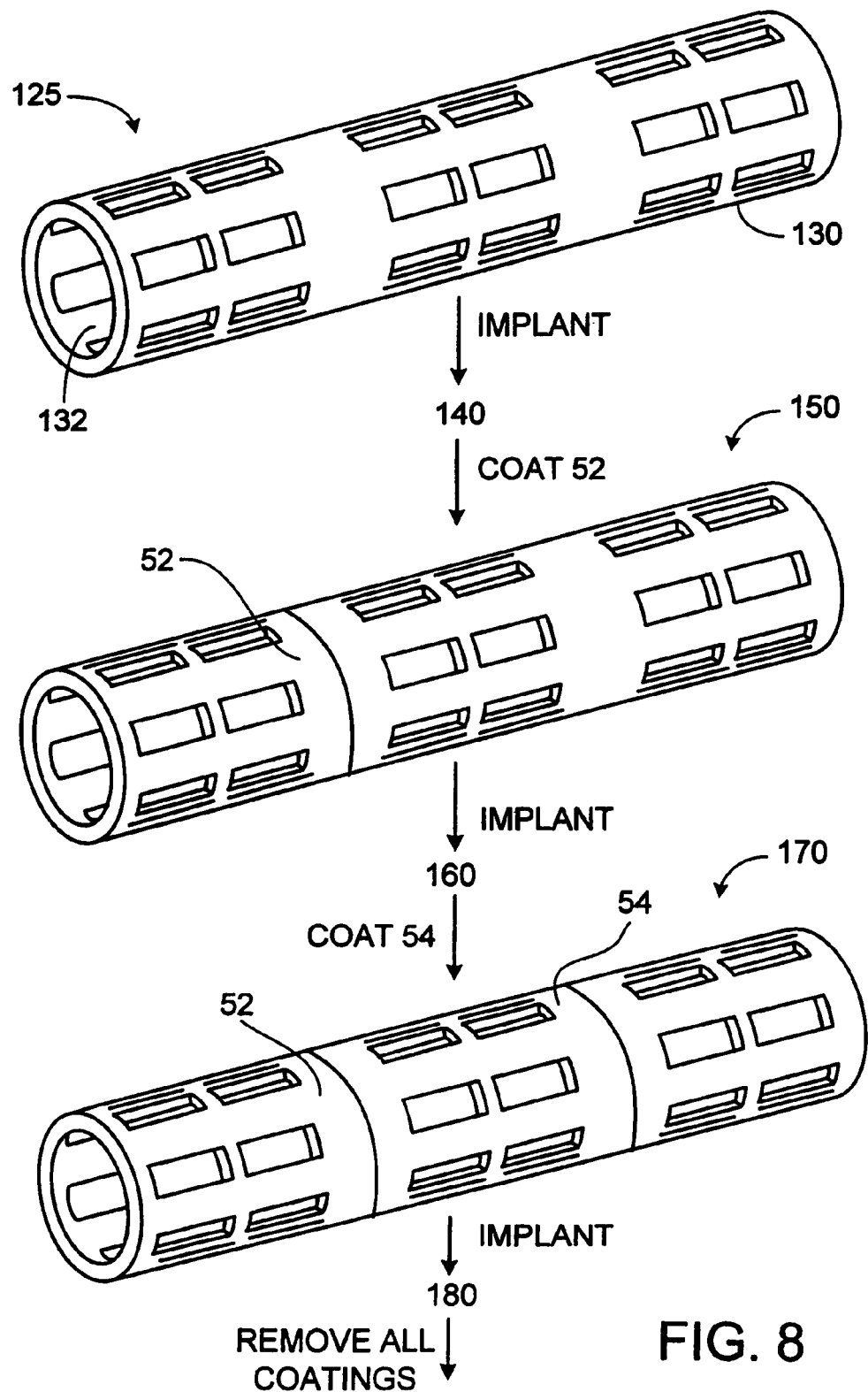
FIG. 8 is a sequence of perspective views illustrating a method of making the stent of FIG. 7.

Referring now to FIG. 8, stent 50 can be produced from a metallic pre-stent 125 by employing system 80 shown in FIG. 5. During production, metallic pre-stent 125 is placed in system 80, where all portions of the pre-stent 125, including outer 130 and inner portions 132, are implanted with a selected species, e.g., oxygen or nitrogen. After a desired implantation time, an implanted pre-stent 140 is removed from system 80. Implanted pre-stent 140 at this point has a transverse cross-section of segment 52 along its entire longitudinal length. Next, all exposed surfaces of segment 52 of implanted pre-stent 140 are covered with a coating, e.g., a protective polymeric coating, such as a styrene-isoprene-butadiene-styrene (SIBS) polymer, to produce a coated pre-stent 150. Coated pre-stent 150 is then placed back into system 80 and implanted with the desired species for the desired time, and then is removed from system 80, to produce a coated pre-stent 160. Conditions for implantation are selected to penetrate the desired species more deeply into pre-stent 150 than during formation of pre-stent 140. The coating on segment 52 protects this segment from additional implantation by the desired species. At this point, segment 52 of coated pre-stent 160 remains unchanged from pre-stent 140 (except for the protective coating), while the remaining portion of pre-stent 160 has a transverse cross-section of segment 54. Next, all exposed surfaces of segment 54 of pre-stent 160 are covered with a coating to produce a coated pre-stent 170. Coated pre-stent 170 is then placed back into system 80 and implanted with the desired species for the desired time, and then is removed from system 80, to produce a coated pre-stent 180. Conditions for implantation are selected to penetrate the desired species more deeply into pre-stent 170 than during formation of pre-stent 160. The coating on segments 52, 54 protects these segments from additional implantation by the desired species. At this point, coated pre-stent 180 has the desired transverse cross sections. The coatings can be removed, e.g., by rinsing with a solvent such as toluene, to complete the production of stent 50. A stent having tapered thicknesses can be produced by masking the interior and/or outer portions with a movable sleeve and longitudinally moving the sleeve and/or the stent relative to each other during implantation.

In use, the stents can be used, e.g., delivered and expanded, using a catheter delivery system, such as a balloon catheter system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Radius® or Symbiot® systems, available from Boston Scientific Scimed, Maple Grove, Minn.

The stents described herein can be of a desired shape and size (e.g., coronary stents, aortic stents, peripheral vascular stents, gastrointestinal stents, urology stents, and neurology stents). Depending on the application, the stent can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. The stents can be balloon-expandable, or a combination of self-expandable and balloon-expandable (e.g., as described in U.S. Pat. No. 5,366,504).

While a number of embodiments have been described above, the invention is not so limited.

As an example, the stents described herein can also be prepared using a laser-driven ion implantation process. Laser-driven ion implantation has been discussed by Yue, *Scripta Materialia,* 38(2), 191-198 (1998); and Schaaf, *Proceedings of SPIE*, vol. 5147, 404-415 (Bellingham, Wash. 2003).

As another example, while the stents may have both outer and inner portions implanted with a desired species, in other embodiments, one or more segments of a stent may have only the outer portion or the inner portion implanted with the desired species.

Outer portions of a pre-stent can be implanted with a desired species during PIII, e.g., by placing a mandrel, a pin or a sleeve that is sized to mate with the selected inner portion(s) of the pre-stent so that during plasma immersion, plasma is effectively blocked from entering inner portions of the pre-stent. Such a stent, after implantation, may have a transverse cross-section that has only two portions: an outer portion that is implanted with the desired species, and an inner portion that has not been implanted. Inner portions of a pre-stent can be implanted with a desired species during PIII, e.g., by placing a polymeric coating on selected outer portion(s) of the pre-stent so that during plasma immersion the desired species can penetrate only the inner portions and is prevented from penetrating the outer portions. Alternatively, outer portions can be protected by placing the pre-stent in a tight-fitting tube, e.g., a heat shrink tube, to cover the outer portions.

In some embodiments, photo-lithography and/or stereo-lithography can be used to mask portions of a pre-stent to prevent implantation.

As another example, while outer and inner portions 20, 26 described herein include, respectively, the outer and inner surfaces of a stent, in other embodiments, one or both of the outer and inner portions are spaced from the outer and inner surfaces, respectively. For example, after one or both of outer and inner portions 20, 26 are formed, a second material can be disposed on one or both of the outer and inner portions, thereby forming a multi-layered stent in which the inner and/or outer portions having the first material(s) are spaced from the surfaces of the stent. The second material can be, for example, an erodible material, such as an erodible element, an erodible alloy, or an erodible polymer. This multi-layered construction can further allow the erosion of the stent to be controlled to provide a desired erosion profile over time.

In some embodiments, the corrosion rate of a bioerodible material can be increased by addition of one or more other materials. As an example, outer and inner portions 20, 26 of tubular body 13 can include an erodible combination of the erodible material of middle portion 24 and one or more first materials capable of increasing the erosion rate. For example, middle portion 24 can be formed of iron, and outer and inner portions 20, 26 can be formed of an alloy of iron and platinum.

Figure 9:
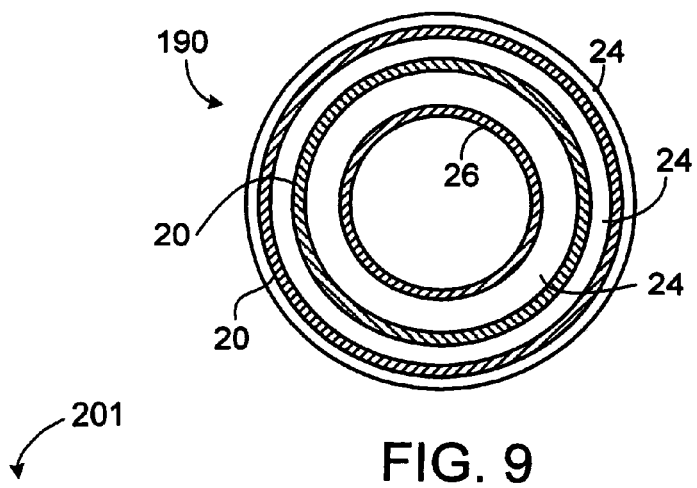
FIG. 9 is a cross-sectional view of an embodiment of an erodible stent.

Referring to FIG. 9, a multi-layered, erodible stent 190 may have more than two (e.g., three, four, five, six or more) outer and/or inner portions 20, 26. This multi-layered construction can provide a stent with an erosion profile resembling a square wave in which the erosion rates alternate between two (or more) different values.

Figure 10:
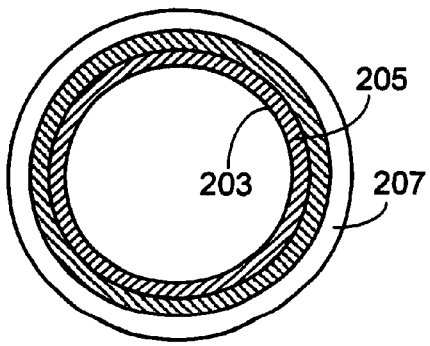
FIG. 10 is a cross-sectional view of an embodiment of an erodible stent.

In some embodiments, a stent can be configured to erode sequentially from an inner surface to an outer surface, or vice versa. FIG. 10 shows an erodible stent 201 having an inner layer 203, a middle layer 205, and an outer layer 207. The compositions and/or thicknesses of layers 203, 205, 207 can be selected as described above to selectively erode stent 201 from inner layer 203, to middle layer 205, and then to outer layer 207. In some embodiments, outer layer 207 can include a non-erodible material, such as a plastically-deformable stainless steel or a superelastic, shape memory material (e.g., Nitinol). This construction allows the stent to support the body vessel initially using the strength of multiple layers, and to reduce in thickness over time (e.g., after cells have endothelialized the stent). The reduction in thickness can enhance the flexibility the stent to better match the natural state of the body vessel.

The stents described herein can be a part of a covered stent or a stent-graft. For example, a stent can include and/or be attached to a biocompatible, non-porous or semi-porous polymer matrix made of polytetrafluoroethylene (PTFE), expanded PTFE, polyethylene, urethane, or polypropylene.

The stents described herein can have non-circular transverse cross-sections. For example, transverse cross-sections can be polygonal, e.g., square, hexagonal or octagonal.

The stents described herein can include non-metallic structural portions, e.g., polymeric portions. The polymeric portions can be erodible. The polymeric portions can be formed from a polymeric alloy. Polymeric stents have been described in U.S. patent application Ser. No. 10/683,314, filed Oct. 10, 2003; and U.S. patent application Ser. No. 10/958,435, filed Oct. 5, 2004, the entire contents of each is hereby incorporated by reference herein.

The stents can include a releasable. therapeutic agent, drug, or a pharmaceutically active compound, such as described in U.S. Pat. No. 5,674,242, U.S. Ser. No. 09/895,415, filed Jul. 2, 2001, U.S. Ser. No. 11/111,509, filed Apr. 21, 2005, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics. The therapeutic agent, drug, or a pharmaceutically active compound can be dispersed in a polymeric coating carried by the stent. The polymeric coating can include more than a single layer. For example, the coating can include two layers, three layers or more layers, e.g., five layers. The therapeutic agent can be a genetic therapeutic agent, a non-genetic therapeutic agent, or cells. Therapeutic agents can be used singularly, or in combination. Therapeutic agents can be, for example, nonionic, or they may be anionic and/or cationic in nature. An example of a therapeutic agent is one that inhibits restenosis, such as paclitaxel. The therapeutic agent can also be used, e.g., to treat and/or inhibit pain, encrustation of the stent or sclerosing or necrosing of a treated lumen. Any of the above coatings and/or polymeric portions can by dyed or rendered radio-opaque.

The stents described herein can be configured for non-vascular lumens. For example, it can be configured for use in the esophagus or the prostate. Other lumens include biliary lumens, hepatic lumens, pancreatic lumens, uretheral lumens and ureteral lumens.

Figure 11:
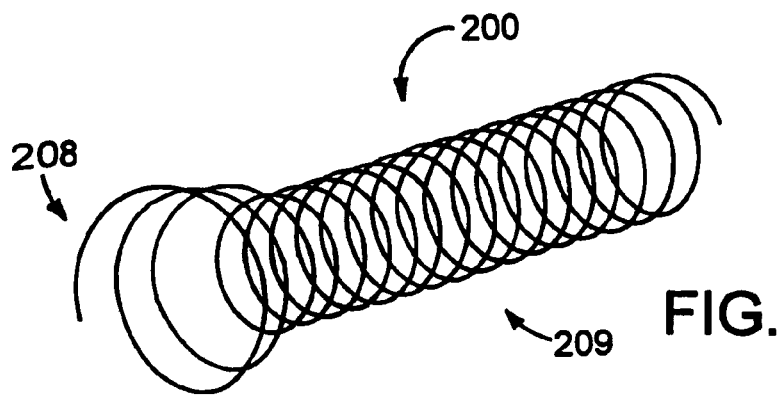
FIG. 11 is a perspective view of an embodiment of an erodible coil stent having a flared end.

Other configurations of stents are also possible. Referring to FIG. 11, a metallic coiled stent 200 has a straight portion 209 and a flared end portion 208. Flared end portion 208 can be have a lower overall erosion rate than straight portion 209, such that straight portion 209 erodes first in a lumen.

Figure 12:
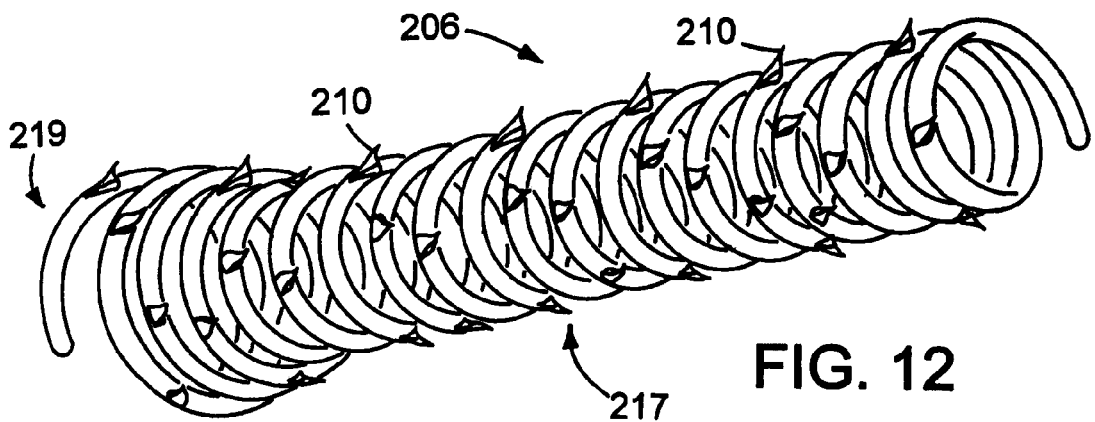
FIG. 12 is a perspective view of an embodiment of an erodible coiled stent having a flared end and engaging elements.

Referring to FIG. 12, a metallic coiled stent 206 has a straight portion 217 and a flared end portion 219. Stent 206 includes a plurality of protruding elements 210 that are integral with and extend outwardly from both portions 217 and 219 of stent 206. The friction provided by the protruding elements can help to hold stent 206 in place within, e.g., the prostatic urethra. Flared end portion 219 and straight portion 2107 can have similar overall erosion rates, while protruding elements 210 can have a lower overall erosion rate to allow the protruding elements to have a lifetime approaching that of the bulk stent 206, e.g., so that frictional control is maintained during the stent's lifetime.

Figure 13:
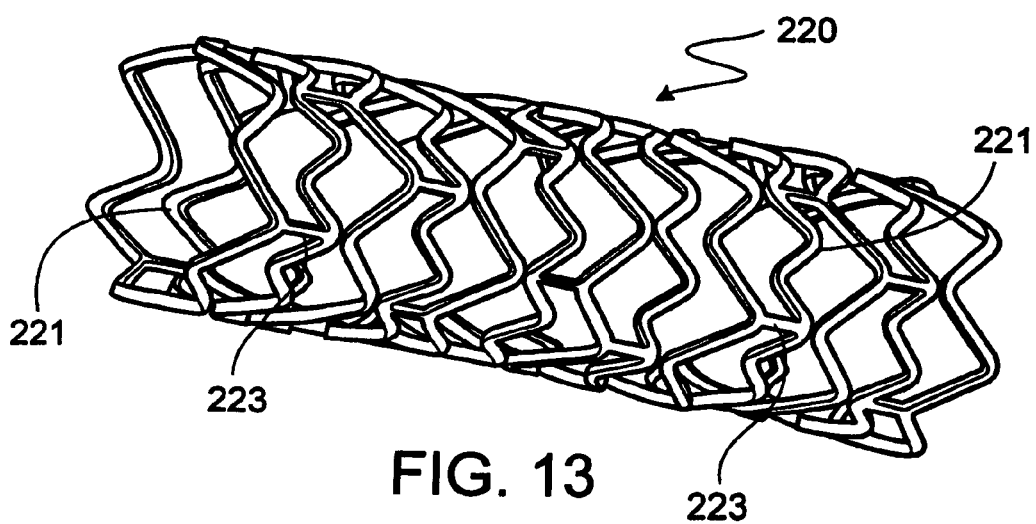
FIG. 13 is a perspective view of an embodiment of an erodible wire stent having bands and connectors that extend between and connect adjacent bands.

Referring to FIG. 13, a metallic erodible wire stent 220 has bands 221 and connectors 223 that extend between and connect adjacent bands 221. Connectors 223 can be have a higher overall erosion rate than bands 221, such that connectors 223 erode first in a lumen. Such a configuration, e.g., enables greater flexibility of the stent as it erodes and ages.

Other embodiments are within the scope of the claims.

What is claimed is:

1. An endoprosthesis comprising:
a first portion having a first erodible metallic composition comprising magnesium or a magnesium alloy, the first portion having a first erosion rate, and a second portion having a second erodible metallic composition comprising an alloy of magnesium and an element selected from the group consisting of nitrogen, carbon, silicon, oxygen, sulfur, chromium, silver, gold, boron, and combinations thereof, the second portion having a second erosion rate slower than the first erosion rate, wherein the second portion is at least an outside surface of the endoprosthesis and the first portion is disposed inwardly of the second portion, the erosion rates being measured by suspending the endoprosthesis in a stream of Ringer's solution flowing at a rate of 0.2 m/second with all surfaces of the endoprosthesis being exposed to the stream of Ringer's solution, said Ringer's solution being a solution of distilled water containing 8.6 gram sodium chloride, 0.3 gram potassium chloride, and 0.33 gram calcium chloride per liter.

2. The endoprosthesis of claim 1, wherein the first erodible metallic composition is substantially pure magnesium.

3. The endoprosthesis of claim 1, wherein the first and second portions are circular in a transverse cross-section of the endoprosthesis.

4. The endoprosthesis of claim 1, wherein a thickness of the second portion is from about 10 nm to about 1000 nm.

5. The endoprosthesis of claim 4, wherein the thickness is from about 15 nm to about 100 nm.

6. The endoprosthesis of claim 1, wherein the erosion rate of the second portion is from about 0.01 percent of an initial mass of that portion per day to about 1 percent of the initial mass of that portion per day.

7. The endoprosthesis of claim 6, wherein the erosion rate is from about 0.1 percent of the initial mass of that portion per day to about 0.5 percent of the initial mass of that portion per day.

8. The endoprosthesis of claim 1, wherein the erosion rate of the second portion is from about 0.2 percent of an initial mass of that portion per day to about 10 percent of the initial mass of that portion per day.

9. The endoprosthesis of claim 8, wherein the erosion rate is from about 0.5 percent of the initial mass of that portion per day to about 5 percent of the initial mass of that portion per day.

10. The endoprosthesis of claim 1, wherein the erosion rate of the first portion is from about ten percent to about one-hundred percent greater than the erosion rate of the metallic portion having the lower erosion rate.

11. The endoprosthesis of claim 1, wherein the first and second portions are disposed within a longitudinal segment of the endoprosthesis.

12. The endoprosthesis of claim 1, wherein the endoprosthesis includes a plurality of segments, each segment including the first portion and the second portion, at least two of the segments having different erosion rates.

13. The endoprosthesis of claim 12, wherein at least two of the segments are arranged along a longitudinal length of the endoprosthesis.

14. The endoprosthesis of claim 1, wherein the endoprosthesis is adapted to erode sequentially along a longitudinal length of the endoprosthesis.

15. The endoprosthesis of claim 1, wherein the endoprosthesis is adapted to erode sequentially along a direction transverse to the longitudinal length of the endoprosthesis.

16. The endoprosthesis of claim 1, comprising an inner surface, an outer surface, and a portion between the inner and outer surfaces, wherein the portion between the inner and outer surfaces has an erosion rate higher than an erosion rate of the inner surface or the outer surface.

17. The endoprosthesis of claim 1, wherein the endoprosthesis is tubular in form.

18. The endoprosthesis of claim 1, wherein the endoprosthesis comprises a stent.

19. The endoprosthesis of claim 1, wherein the second portion completely surrounds the first portion.

20. A method of making a bioerodible endoprosthesis, the method comprising:
implanting a material into a portion of a magnesium or magnesium alloy endoprosthesis, or precursor thereof, to create a bioerodible endoprosthesis comprising a first portion having a first metallic composition comprising the magnesium or the magnesium alloy and a second portion comprising an alloy of magnesium with the implanted material, wherein the implanted material comprises an element selected from the group consisting of nitrogen, carbon, silicon, oxygen, sulfur, chromium, silver, gold, boron, and combinations thereof, wherein the second portion is at least an outside surface of the endoprosthesis and the first portion is disposed inwardly of the second portion, wherein the second portion has a slower erosion rate than the first portion, the erosion rates being measured by suspending the endoprosthesis in a stream of Ringer's solution flowing at a rate of 0.2 m/second with all surfaces of the endoprosthesis being exposed to the stream of Ringer's solution, said Ringer's solution being a solution of distilled water containing 8.6 gram sodium chloride, 0.3 gram potassium chloride, and 0.33 gram calcium chloride per liter.

21. The method of claim 20, wherein the implanting employs a plasma.

22. The method of claim 20, further comprising, prior to implanting, applying a shielding to a portion of the endoprosthesis.

23. The method of claim 22, wherein the shielding comprises a coating.

24. The method of claim 23, wherein the coating comprises a polymer.

25. The method of claim 22, further comprising, after implanting, removing the applied shielding.

26. The method of claim 20, wherein the second portion completely surrounds the first portion.

* * * * *